United States Patent
Dinauer et al.

(10) Patent No.: US 12,162,663 B2
(45) Date of Patent: Dec. 10, 2024

(54) FUNCTIONAL LAMINATE PACKAGING AND METHOD OF MANUFACTURE

(71) Applicant: LasX Industries, Inc., Saint Paul, MN (US)

(72) Inventors: Ethan Dinauer, Saint Paul, MN (US); Doug Bryant, Mendota Heights, MN (US); William Todd Bedwell, Hayward, WI (US); Scott Hellquist, White Bear Lake, MN (US); Michael Sticha, South Saint Paul, MN (US)

(73) Assignee: LasX Industries, Inc., Saint Paul, MN (US)

( * ) Notice: Subject to any disclaimer, the term of this patent is extended or adjusted under 35 U.S.C. 154(b) by 130 days.

(21) Appl. No.: 17/695,576

(22) Filed: Mar. 15, 2022

(65) Prior Publication Data

US 2022/0289448 A1 Sep. 15, 2022

Related U.S. Application Data

(60) Provisional application No. 63/161,341, filed on Mar. 15, 2021.

(51) Int. Cl.
*B65D 75/30* (2006.01)
*A61B 50/30* (2016.01)

(52) U.S. Cl.
CPC ............. *B65D 75/30* (2013.01); *A61B 50/30* (2016.02); *B65D 2203/02* (2013.01); *B65D 2575/30* (2013.01)

(58) Field of Classification Search
CPC ................ B65D 75/30; B65D 2203/02; B65D 2575/30; A61B 50/30

USPC ..... 435/288.3, 288.4, 288.5, 287.8; 206/484, 206/484.2
See application file for complete search history.

(56) References Cited

U.S. PATENT DOCUMENTS

| | | | | |
|---|---|---|---|---|
| 5,821,073 A | * | 10/1998 | Lee | G01N 33/558 436/514 |
| 6,991,940 B2 | * | 1/2006 | Carroll | G01N 33/525 436/805 |
| 8,313,699 B2 | * | 11/2012 | Kretschmann | G01N 31/226 422/50 |
| 8,518,342 B2 | * | 8/2013 | Mosticone | B01L 3/505 422/50 |
| 8,968,677 B2 | * | 3/2015 | LaBorde | G01N 33/50 435/287.7 |
| 2009/0151864 A1 | | 6/2009 | Burke et al. | |
| 2009/0263854 A1 | | 10/2009 | Jacono et al. | |
| 2010/0028937 A1 | * | 2/2010 | Liu | G01N 33/526 435/287.8 |
| 2012/0282636 A1 | * | 11/2012 | Altschul | G01N 33/525 422/69 |

(Continued)

OTHER PUBLICATIONS

PCT International Search Report, International Application No. PCT/US22/20394 (Date of Mailing Jul. 6, 2022).

*Primary Examiner* — Jacob K Ackun
(74) *Attorney, Agent, or Firm* — Campbell IP Law LLC

(57) ABSTRACT

A functional laminate package comprises a bottom layer, a top layer comprising an opening, and an intermediate layer disposed between the bottom layer and the top layer and comprising a void configured to house a package content, the void in communication with the opening in the top layer, and a removable label affixed to the top layer covering the opening.

16 Claims, 16 Drawing Sheets

(56) References Cited

U.S. PATENT DOCUMENTS

2014/0154786 A1 6/2014 LaBarre et al.
2016/0167042 A1 6/2016 Tyrrell et al.
2016/0282343 A1 9/2016 Jeyendran et al.

* cited by examiner

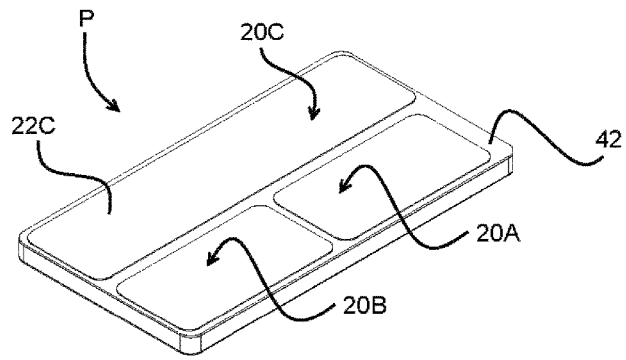
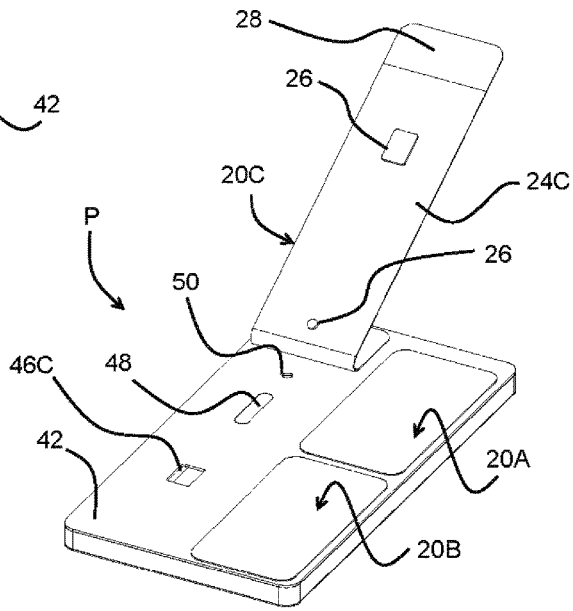
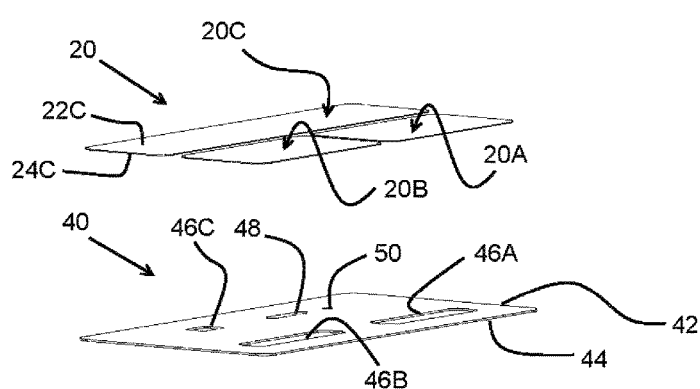
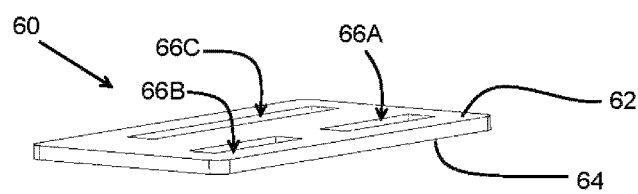
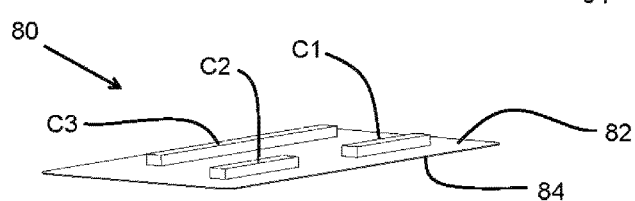
FIG. 3A
FIG. 3B
FIG. 3C

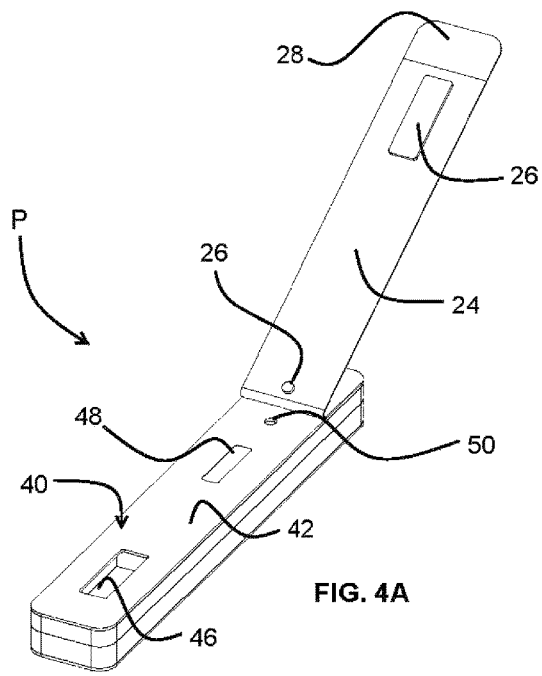
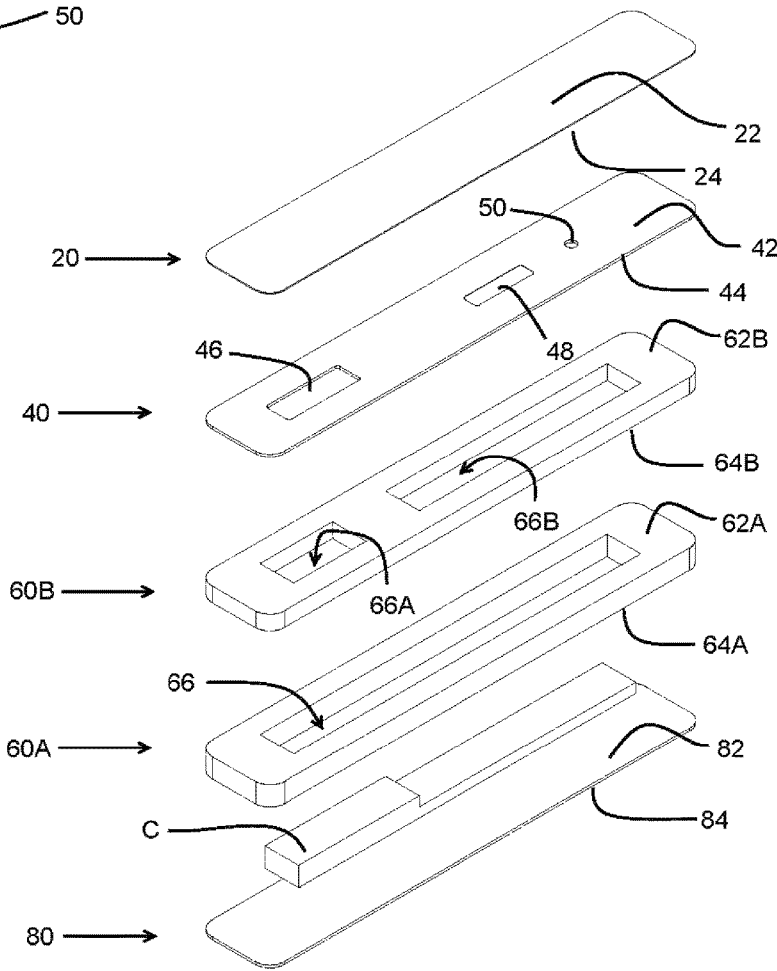
FIG. 4A
FIG. 4B

FUNCTIONAL LAMINATE PACKAGING AND METHOD OF MANUFACTURE

PRIORITY CLAIMS

This application claims the benefit of U.S. provisional patent application No. 63/161,341 filed Mar. 15, 2021, the entirety of which is hereby incorporated by reference into this application.

BACKGROUND

The present disclosure relates in general to methods and compositions for producing packaging, and more particularly, to single-use disposable packaging for housing in-vitro diagnostics, assays, and solid or liquid chemicals and reagents, among other uses.

Small disposable in-vitro diagnostic tests, such as lateral flow assays (LFAs), are typically housed in a hard molded or injection molded plastic cassette. Although the LFA is typically produced using a high-speed roll-to-roll process, the use of plastic cassettes requires a separate assembly process wherein each LFA is placed inside a plastic cassette, and then over-packaging is used to package the entire LFA-cassette assembly and protect it from the environment. Additionally, printed instructions are sometimes provided as a separate booklet or insert into the packaging, or otherwise printed on the outside of the packaging, because the plastic molded cassette does not provide sufficient surface area or flat features for printing.

Other in-vitro diagnostic tests or assays are often provided as a packaged kit, such as a box, with each reagent and tool provided in separate plastic packaging along with a printed instruction booklet, requiring the user to study the instructions and use each component carefully and in the right order to successfully execute the assay. Where numerous reagent vials and components are provided for a multi-step process, the potential for user error is compounded.

Otherwise, packaging for liquid or solid form chemicals and reagents are often provided in packaging made via a form-fill-seal method, presenting some of the same printing and inefficiency in manufacturing problems as stated above compared to roll-to-roll processes.

Accordingly, there is a need for in-vitro diagnostic tests and assays which are user friendly, provide a printable surface for instructions or other valuable information, are optimized to reduce package waste from over-packing, and are amenable to high-speed roll-to-roll and in-line manufacturing processes.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

The present disclosure relates to a laminate package comprising a bottom layer, a top layer, and an intermediate layer disposed therebetween. The intermediate layer comprises a void for housing a package content, and the top layer comprises one or more openings in communication with the void. An adhesive label may be affixed to the top layer to cover the one or more openings.

In another aspect, the present disclosure relates to a functional laminate package comprising a plurality of laminated layers including a void in at least one of the layers configured to functionally house a package content; an opening in the package in fluid communication with the void and the package content, and wherein the package content is affixed to one of the plurality of laminated layers.

BRIEF DESCRIPTION OF THE DRAWINGS

FIG. 3A is an isometric view of a functional package according to the present disclosure.

FIG. 3B is an isometric view of the functional package of FIG. 3A, showing a label peeled back.

FIG. 3C is an isometric exploded view of the layers of the functional package of FIGS. 3A and 3B.

FIG. 4A and in isometric view of a functional package according to the present disclosure, showing a label peeled back.

FIG. 4B is an isometric exploded view of the layers of the functional package of FIG. 4A.

DETAILED DESCRIPTION

Figures 1A, 1B:
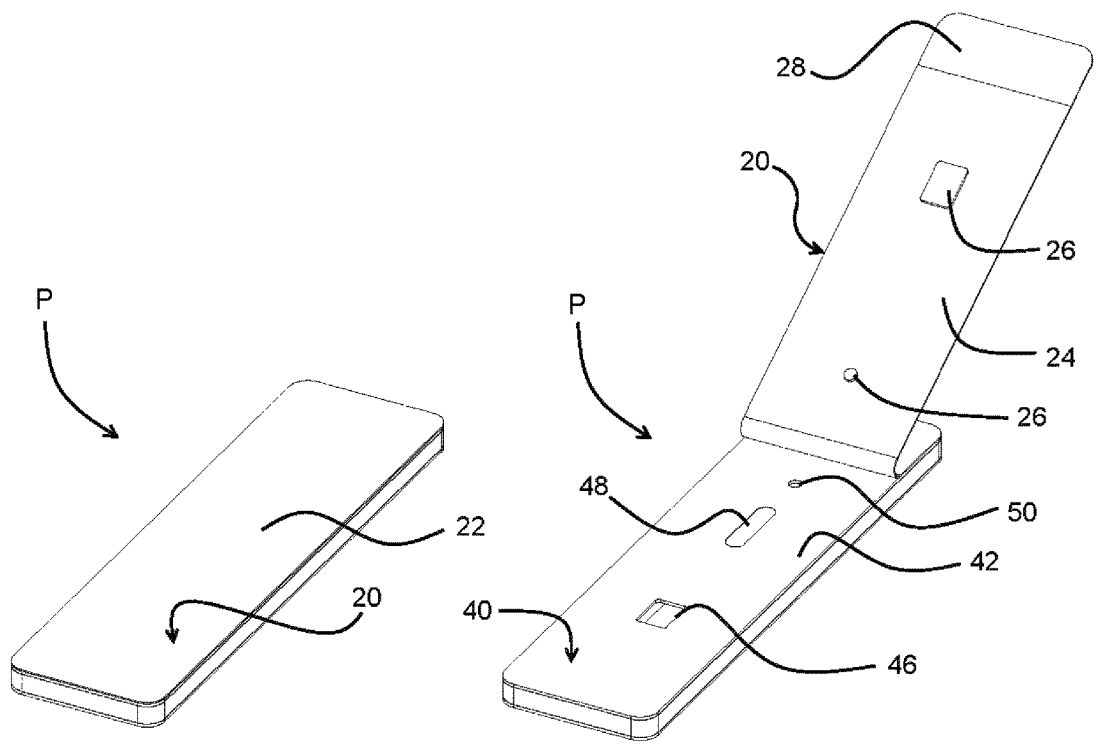
FIG. 1A is an isometric view of a functional package according to the present disclosure.
FIG. 1B is an isometric view of the functional package of FIG. 1A showing a label peeled back.

Disclosed herein is a functional laminate packaging and method of manufacture, providing numerous advantages over the state of the prior art, including but not limited to high-speed roll-to-roll manufacturing capability and in-line processing capability, reduced package waste, large and customizable printable areas, and improved freedom of design and functionality for a wide variety of end-use applications. The package of the present disclosure comprises web-based layered materials to form a highly configurable laminate structure, and may be flexibly designed to functionally house any content compatible with high-speed roll-to-roll manufacturing processes and placement. As an example, suitable package contents may include but are not limited to in-vitro diagnostic devices and assays; lateral flow assays (LFAs); lab on a chip; diagnostic test strips; microfluidics; biosensors; liquid or solid chemicals and reagents; power supplies (e.g., batteries); and circuitry.

In one aspect, a laminate package according to the present disclosure comprises a bottom layer, a top layer, and an intermediate layer disposed therebetween. The intermediate layer comprises a void for housing a package content, and the top layer comprises one or more openings in communication with the void. An adhesive label may be affixed to the top layer to cover the one or more openings.

In another aspect, a functional laminate package comprises a plurality of laminated layers including a void in at least one of the layers configured to functionally house a package content, an opening in the package in fluid communication with the void and the package content, and wherein the package content is affixed to one of the plurality of laminated layers.

In another aspect, the one or more openings may be kiss cut through the top layer and into the bottom adhesive surface of the label. Accordingly, when the label is peeled back or otherwise removed from the top layer, the kiss cut material is also pulled away with the label and removed from the top layer, thereby exposing the one or more openings in the top layer and providing access to the void in the intermediate layer.

In another aspect, a portion of the top layer may be kiss cut to form a gate or dam adjacent to a reservoir formed in the top layer. In such case, when the label is peeled back or otherwise removed from the top layer, the kiss cut gate material of the top layer is also pulled away with the label and removed, thereby exposing a channel or other designed feature to allow fluid to flow in or out of a reservoir. For example, this may facilitate the flow of reagents, biological samples or other substances from one void to another in the laminate package structure as described in more detail below.

In another aspect, the dimensions of the void in the intermediate layer may be configured to suitably house a package content. Importantly, the void may be configured to enhance or at least maintain (i.e. not interfere) with the function of the package content, in other words, it functionally houses the content rather than merely containing it for transport. For example, if the package content is an LFA, the dimensions of the void may be configured to provide suitable clearance between the walls of the void and the LFA such that the function of the LFA is not disturbed if the package is bent, compressed or otherwise distorted. In another example, if the package content comprises a liquid or solid substance, such as a chemical or reagent, then the dimensions of the void may be configured to provide an appropriate amount of the substance such that it fills the void. In another aspect, the dimensions of the void may be configured to enable a press-fit of the package content into the void without requiring the use of adhesives or other bonding agents.

In another aspect, an appropriately sized and designed breakable vial may be utilized to contain a chemical or reagent content, particularly where such content may not be chemically or physically compatible with the material of the package and layers. In such case, the breakable vial may be placed within a void of an intermediate layer, and the laminate package is configured to have adequate flexibility or compressibility, such that the vial can be crushed or otherwise broken inside the package through compressing or squeezing a pressure point on the package or bending the package to release the contents into the void or an adjacent void.

In another aspect, the package content may be stably affixed, such as by an adhesive or other bonding technique, to the top surface of the bottom layer, and in a manner suitably positioning the package content within the void of an intermediate layer. For sensitive package contents, like an LFA or other in-vitro diagnostic device, the stable bond to the bottom layer may prevent the contents from moving around and getting damaged when the package is transported or handled.

In another aspect, where a package content comprises an irregular or uneven surface topology, protrusions or other prominent features, a second intermediate layer may be utilized comprising a second void configured to accommodate such features. Alternatively, numerous intermediate layers may be laminated between the top and bottom layers of the package, each with one or more voids spatially related and configured to accommodate the features of the packaged content, including to isolate any portion of the packaged content for receiving a sample, for example.

In another aspect, a first void of an intermediate layer may be in communication with a second void of an intermediate layer via a channel, passageway or other structure. A plurality of voids may reside in the same intermediate layer and communicate laterally within the single layer, or may reside in separate intermediate layers and communicate vertically between the multiple layers, or both. This may enable, for example, the flow of reagents, biological samples or other substances from one void to another, facilitating functional and fluid communication or interaction between housed package contents including chemical reagents, in-vitro diagnostic devices or other non-limiting examples previously described above.

In another aspect, the removable label may be printed with information relating to the package design, ownership, identity, package content, function, or use, as non-limiting examples. This may include, for example, information identifying the package contents or diagnostic assay, instructions for utilizing functional aspects of the package and/or contents, marketing and brand information (e.g., trademarks), bar codes (e.g., stock-keeping units), product safety information, and more. Alternatively, the bottom surface of the bottom layer may also be printed with such information, alone or in combination with the label. In another example, the top surface of the top layer may also be printed with information, such that it is revealed when the label is removed. Due to the roll-to-roll manufacture and web-based layers, any layer could be flexibly printed with useful information relating to the package, including but not limited to user-facing information such as instructions and warnings, as well as manufacturer related information such as registration marks, product or content identifying information and others.

In another aspect, two or more separate labels may cover separate openings in communication with separate voids housing separate package contents or components within the same package. For example, to provide for a test kit where separate components must be utilized in a sequential manner, printed information on various parts of the package as described above may be utilized to clearly guide the user through the sequence for performing an assay and utilizing each component, thereby minimizing the chance of user error.

In another aspect, functional features such as communicating voids and kiss-cut gates may be utilized in combination with two or more separate labels and instructional information to provide a highly functionalized package for performing multi-step sequential assays in a user friendly, convenient manner.

In another aspect, a tamper resistant or tamper evident label may be utilized to ensure the package contents are safe.

In another aspect, a resealable label may be utilized such that any sample placed within the package may be appropriately isolated and handled, including safe disposal of biological samples or reagents, or alternatively enabling the ability to mail samples to another location for further processing or testing.

In another aspect, the environment within the package may be sealed or modified from the external environment, including use of atmosphere controlling substances including but not limited to desiccants and humectants.

Accordingly, it may be appreciated that any combination of the above non-limiting examples of features and designs, including as hereinafter described, may be combined in a single functional package to allow for unprecedented freedom of design for almost any end-use application, but with the many advantages of roll-to-roll manufacture among others.

Figure 1C:
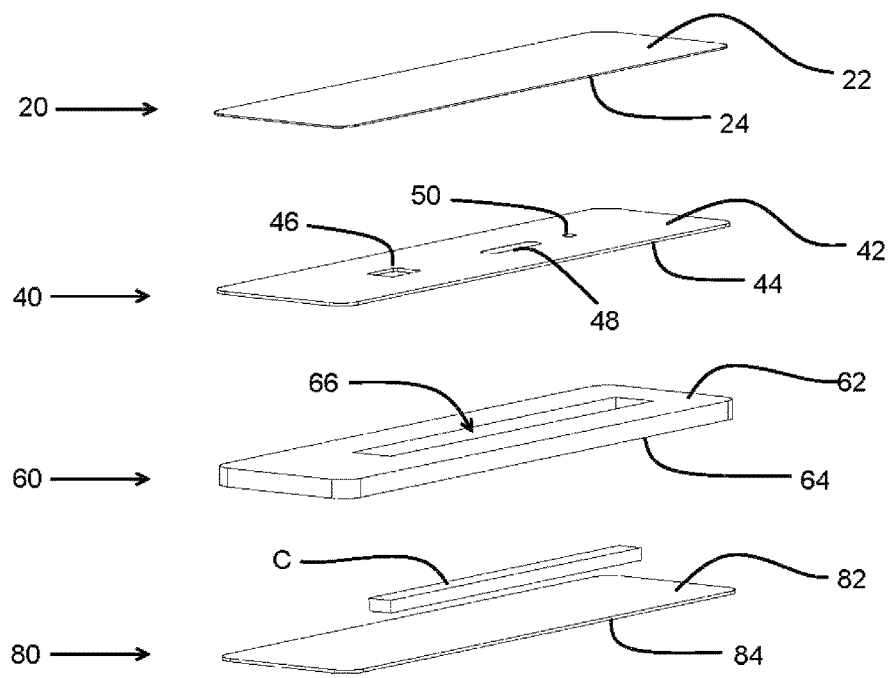
FIG. 1C is an isometric exploded view of the layers of the functional package of FIGS. 1A and 1B.

FIGS. 1A and 1B are isometric views of an example package P according to the present disclosure, showing the package closed in FIG. 1A, and the package open with label 20 peeled away in FIG. 1B. FIG. 1C is an isometric exploded view of each separate layer of package P, showing label 20 having top surface 22 and bottom surface 24; top layer 40 having top surface 42 and bottom surface 44, opening 46, window 48 and vent 50; intermediate layer 60 having top surface 62 and bottom surface 64 as well as void 66; and bottom layer 80 having top surface 82 and bottom surface 84. Further shown is package content C for being housed inside of package P, such as in void 66.

As shown in FIG. 1B, when label 20 is peeled away from top layer 40, then opening 46, window 48 and vent 50 are revealed. Further shown is kiss cut material 26 adhered to the bottom surface 24 of label 20, which represents the material of top layer 40 that was kiss cut against label 20 to form opening 46 and vent 50 and removed when the label 20 was peeled away. Additionally, easy peel zone 28, such as an adhesive deadening zone, on label 20 is optionally provided to facilitate separating and peeling of label 20 away from the top surface 42 by a user.

Opening 46 provides communication between the package P external environment and the internal environment of void 66 inside intermediate layer 60. This is further shown in the detail of the cross-sectional view of FIG. 1F, which is a cross section C-C of package P shown in FIG. 1E (showing top view of package P). Where a package content C is an in-vitro diagnostic device, for example, opening 46 may function as a sample port, allowing for a biological sample to be placed into void 66 and in contact with the device. In such case, opening 46 may be sized appropriately to allow a sample to be pipetted, dripped, poured or otherwise passed through to communicate with package content C inside void 66. Depending on the requirements of the particular end-use application and package content C, vent 50 may be optionally provided to equalize pressure between void 66 and the external environment, thereby preventing or minimizing condensation on the package content C device or window 48, while also facilitating unimpeded movement of a liquid sample specimen through opening 46 or in a housed device by minimizing any backpressure. For example, where package content C is an LFA, LFAs can be humidity sensitive and rely on passive micro-pumping, thus providing vent 50 may help mitigate the sudden rise in humidity that occurs where a body-temperature biological sample is placed inside void 66 to contact the LFA while also ensuring the pressure equalization necessary for unimpeded micro-pumping.

As shown with reference to FIG. 1B for example, window 48 may be provided in top layer 42 and may comprise either a transparent portion of top layer 42, or may alternatively comprise a kiss-cut opening similar to opening 46. Window 48 is provided where a user needs to see the package content C, for example, where an in-vitro diagnostic device, such as an LFA, shows the result of an assay. In such case, window 48 is configured to align with the appropriate portion of the assay display portion of package content C. To further facilitate this alignment, the package content C may be stably affixed, adhered or otherwise bonded to the top surface 82 of the bottom layer 80 to prevent the content C, such as an LFA, from shifting or moving around inside void 66 during transport or handling.

Figure 1D:
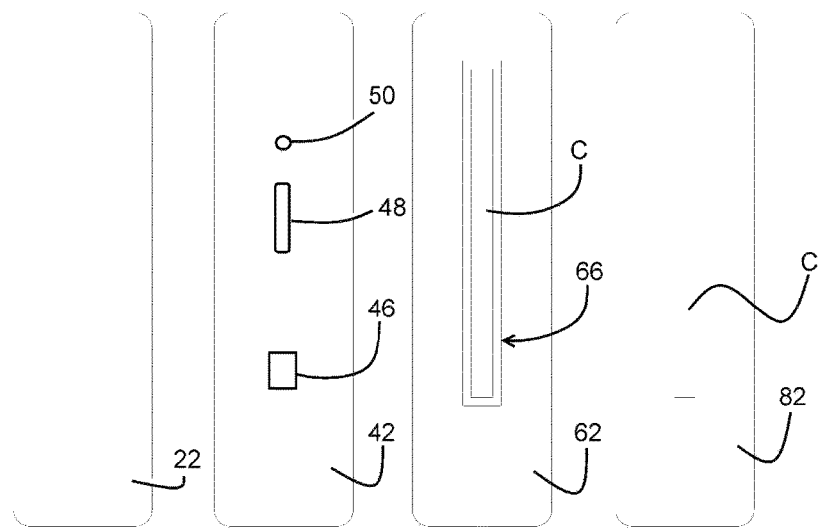
FIG. 1D is a layer-by-layer process view of the functional package of FIGS. 1A-1C.
Figure 1E:
FIG. 1E is a top view of the functional package of FIGS. 1A-1C, showing location of cross section C-C.
Figure 1F:
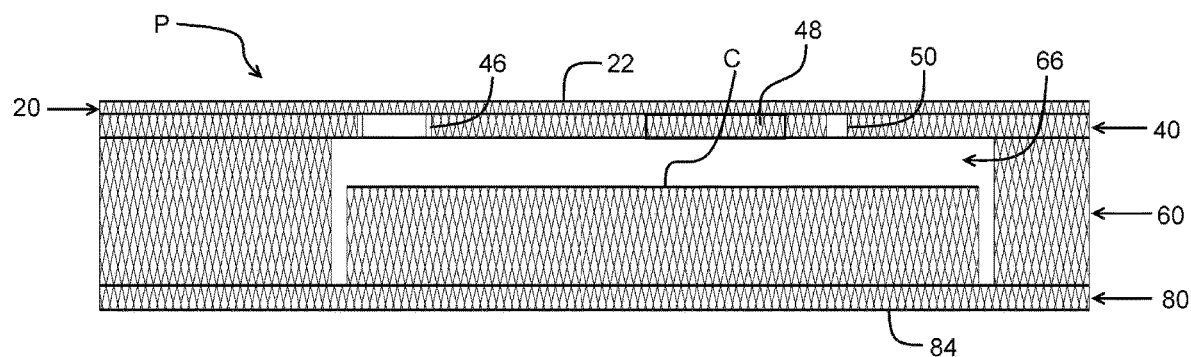
FIG. 1F is a cross-sectional view C-C of FIG. 1E.

FIG. 1D shows an example of a layer-by-layer process of producing the laminate design of package P to house content C, sequenced generally from right to left, and which may also be understood with reference to FIG. 1C sequenced generally from bottom to top. However, these are non-limiting examples, and as may be appreciated by someone skilled in the art of roll-to-roll manufacturing, the order and method of processing, printing and laminating separate web-based materials is highly flexible and customizable and dependent on machine design, speed and productivity requirements, cost and other factors. In one example, content C may be stably affixed on an adhesive top surface 82 of bottom layer 80. The bottom surface 64 of intermediate layer may then be affixed onto the adhesive top surface 82 of bottom layer 80 such that void 66 surrounds content C. Next, an adhesive top surface 62 of the intermediate layer 60 may be affixed to the bottom surface 44 of the top layer 40. Finally, an adhesive bottom surface 24 of label 20 may be affixed on the top surface 42 of top layer 40. Alternatively, the void 66 may also be configured to enable a press-fit of the content C into the void, with or without use of adhesive depending on the stability of the fit.

Alternatively, to facilitate a kiss cut such as described previously, the label 20 and top layer 40 may be first laminated and processed separately from the bottom layer 80, intermediate layer 60 and package content C, with a kiss cut performed through the top layer 40 against the adhesive bottom surface 24 of label 20 to prepare opening 46 and optionally vent 50, and then affixing the bottom surface 44 of the top layer 40 to the adhesive top surface 62 of the intermediate layer 60.

The surface on which adhesive is provided is important in relation to the function of the designed package and package content. For example, by strategically providing adhesive on the adhesive top surface 82 of bottom layer 80 of package P, this enables both the securement of content C onto the bottom layer 80 web during roll-to-roll manufacture in addition to the lamination of intermediate layer 60 onto the same web. This also makes it easier to stably affix any package content C onto the bottom layer 80 web in a case where certain content C may be difficult or inefficient to apply adhesive to separately.

As another example, by strategically providing adhesive on the top surface 62 of the intermediate layer 60, the bottom surface 44 of top layer 40 does not present any adhesive on the portion facing the void 66 in intermediate layer 60, therefore reducing the risk that package content C will stick to top layer 40 in case the package P were bent or distorted or jostled around. Further, in the case of a specimen or sample to be introduced into the void, this also ensures that none of the sample will get stuck to the bottom surface 44 of the top layer facing the void 66 and package content C.

Suitable methods for performing the kiss cut include but are not limited to laser scoring and die cutting. Suitable methods for creating void 66 in intermediate layer include but are not limited to laser scoring or die cutting, though die cutting is preferable in a case where the intermediate layer comprises a suitable foam.

Suitable materials for the top layer 40 and bottom layer 80 include but are not limited to polyethylene terephthalate (PET), polyethylene (PE), high-density polyethylene (HDPE), low-density polyethylene (LDPE), or polypropylene (PP), but may comprise any web-based polymer material capable of adhesive bonding and suitable lamination, and with environmental barrier properties suitable for the package content C.

Suitable materials for intermediate layer 60 may include any sheet-based foam, including but not limited to extruded sheet foam, available in roll format and having environmental barrier properties suitable with package content C, and which is chemically or physically compatible with the package content and any specimen to be introduced into void 66. Additionally, depending on the functional and physical specification of the package to be produced as well as requirements for package content C, foam may be configured for appropriate compression set, compression strength, density, tensile strength, insulative property, shore hardness, low VOC emissions, thermal stability, surface tension, surface wetting, and adhesive peel strength, among other factors. In some embodiments, the foam may comprise a closed cell foam in order to provide better barrier and other properties to the package, or alternatively may comprise an open cell foam where gas transfer and breathability are desired, for example.

Accordingly, selection of materials for each layer, physical and mechanical performance properties, and dimensions (including thickness), may be freely selected based on the physical and functional specifications of the package P to be produced and requirements of content C, including desired rigidity versus flexibility in relation to the package content C, among other factors. By choosing an appropriate sheet foam in roll format for the intermediate layer 60, a high degree of design freedom is enabled with a wide range of choices of thickness and physical properties, such that almost any size void of any configuration and geometry to accommodate almost any package content C may be produced within the web and laminated into the final package P structure.

Suitable methods for laminating the structures of package P are known in the art, and are taught, for example, in the disclosure of U.S. Pat. No. 8,016,963 "Precision Lamination of Multilayered Structures" by Klingbeil et al. and assigned to Lasx Industries, Inc, the entire disclosure of which, except for any definitions, disclaimers, disavowals, and inconsistencies, is incorporated herein by reference. Suitable bonding methods for laminating the layers of package P, or positioning content C onto bottom layer 80, may include but are not limited to adhesive, thermal, and ultrasonic techniques. In case of adhesive, adhesive type and properties may be freely chosen based on the physical and functional specifications of package P to be produced, and the nature of the package layer substrate to be coated. For example, in the case of securing a package content C onto the bottom layer 80, such adhesive should optimally be compatible with both package content C as well as intermediate layer 60 material to prevent delamination either if package P were bent or otherwise distorted or during the user peeling away the label. In case of label 20, adhesive should be of sufficient bond strength to prevent delamination from top layer 40 top surface 42 during storage, transport, and handling, and with sufficient bond strength to pull away any kiss cut material 26 from top layer 40, but in balance with being sufficiently weak so that label 20 does not rip or tear apart when peeled away from top surface 42.

Any package content C may be placed within a void 66 of package P or onto a web of the package P, such as bottom layer 80, via known methods. Where package content P comprises a discreet part, for example, current state of the art automation methods to place discrete parts into high-speed web-based packaging can be accomplished by using a rotary pick and place mechanism. Discrete parts can be placed in bulk into a traditional bowl feeder or centrifugal feeder.

The parts may be accumulated end to end and moved up a vibratory track and then singulated for picking. For slower web speeds, the rotary mechanism could involve a pinion gear moving around the inside of a ring gear that moves a high-speed kinematic motion to vacuum-pick discrete stationary parts. The mechanism acquires the parts and moves them at web speed to place the parts into a void 66 in the web just prior to the top web sealing over the top of the package. For higher speed applications, for example discrete parts can be vibratory fed into a rotary vacuum roller that vacuum picks the parts one at a time, speeding up the parts to web speed as it rotates into tangential contact with the void 66 in the web. When the part is in position a slight air blast reverses the vacuum hold on the part placing the part into a void 66 in the web just prior to the top layer 40 of the web closing over the package.

Where package content C comprises a liquid and powder, for example, a dispense tip may be located over the void 66 and follows the speed of the web during dispensing. Multiple tips can be used over multiple voids 66 depending on the speed and the time duration of the dispense. The tips can be stationary, or index and follow syncing the tip to the web velocity during the dispense and then retreat and follow again for the next dispense. In all cases, the top layer 40 of the web is introduced after the dispense of liquid or powder to close or seal the package P.

Figure 2A:
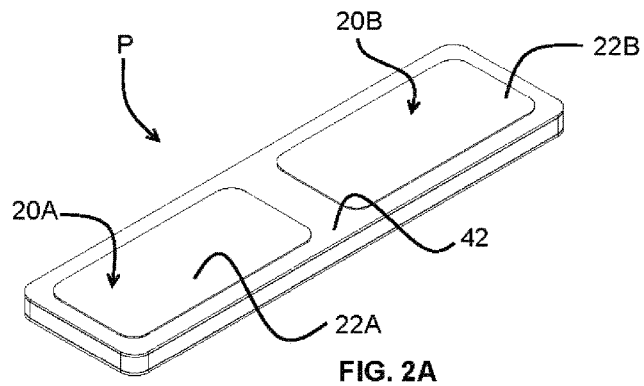
FIG. 2A is an isometric view of a functional package according to the present disclosure.
Figure 2B:
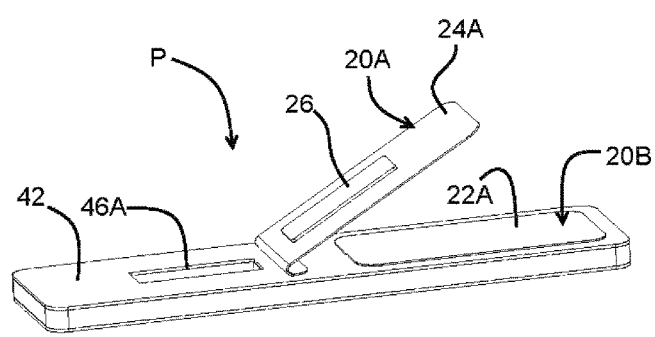
FIG. 2B is an isometric view of the functional package of FIG. 2A showing a label peeled back.
Figure 2C:
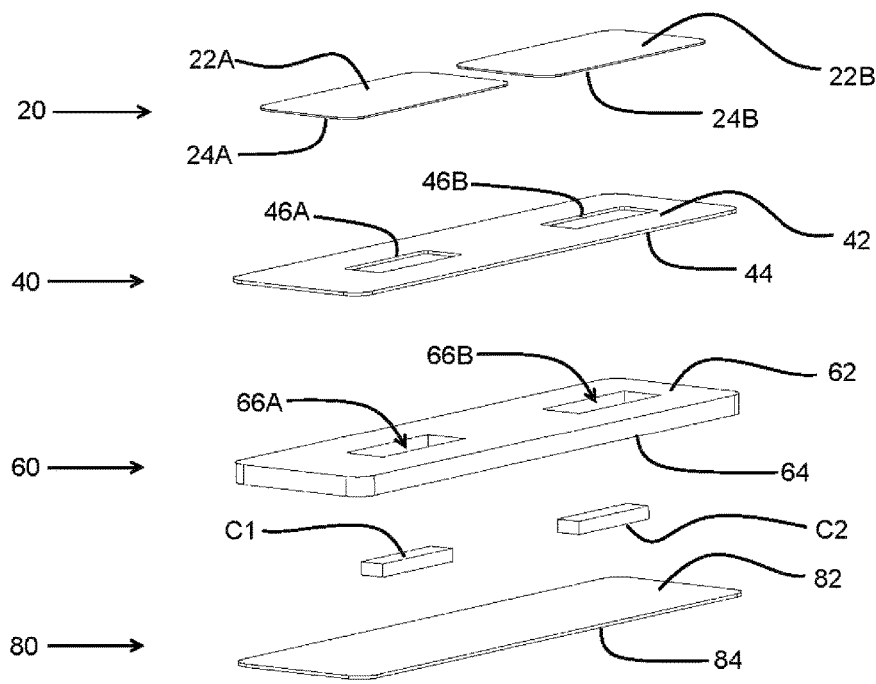
FIG. 2C is an isometric exploded view of the layers of the functional package of FIGS. 2A and 2B.

FIGS. 2A and 2B are isometric views of another example package P according to the present disclosure, and FIG. 2C is an isometric exploded view, wherein a first label 20A and a second label 20B (having top surface 22A, 22B, and bottom surface 24A, 24B, respectively) are provided to cover a first opening 46A and a second opening 46B, respectively, in top layer 40. Each label 20A, 20B may be sequentially peeled away or otherwise removed from the top layer 40 as shown in FIG. 2B with respect to first label 20A. Each of first opening 46A and second opening 46B are in communication with a first void 66A and a second void 66B, respectively, disposed in the intermediate layer 60. As described with reference to the package of FIGS. 1A-1F, kiss cut material 26 may likewise be utilized to form openings 46A and 46B when labels 20A and 20B are peeled away. Further, each of the first void 66A and second void 66B may independently house a first package content C1 and a second package content C2 as shown.

First opening 46A and second opening 46B provide communication between the package P external environment and the internal environment of separate first void 66A and second void 66B inside intermediate layer 60. This is further shown in the detail of the cross-sectional view of FIG. 2F, which is a cross section A-A of the package P shown in FIG. 2E (showing a top view of the package P). Openings 46A, 46B may be sized appropriately depending on the desired function in relation to package contents C1, C2. For example, if package content C1 in first void 66A is a sample collection tool, such as a nasal or throat swab, finger lancet or other sample specimen collecting device, then first opening 46A may be sized large enough to remove the tool by a user's fingers. In another example, if package content C2 in second void 66B is a reagent or diagnostic assay device, then second opening 46B may be sized for insertion of the tool, such as a swab end into the second void 66B and in contact with package content C2 to perform the assay.

Alternatively, package content C1 and C2 may comprise the same, duplicate contents, or any potential combination of separate contents or components. Accordingly, package P of FIGS. 2A-2F may provide for a multi-component diagnostic test kit, and printed information on the top surface 62 of each label 20A, 20B may instruct or otherwise guide the user, including for example the sequence in which to perform the steps of the diagnostic test in relation to contents C1 and C2. Although two functional voids 66A, 66B are shown in this example, any number of voids in intermediate layer 60 may be envisioned according to the number of package contents and desired functionality of the package P, as described with reference to additional Figures of the disclosure below.

Figure 2D:
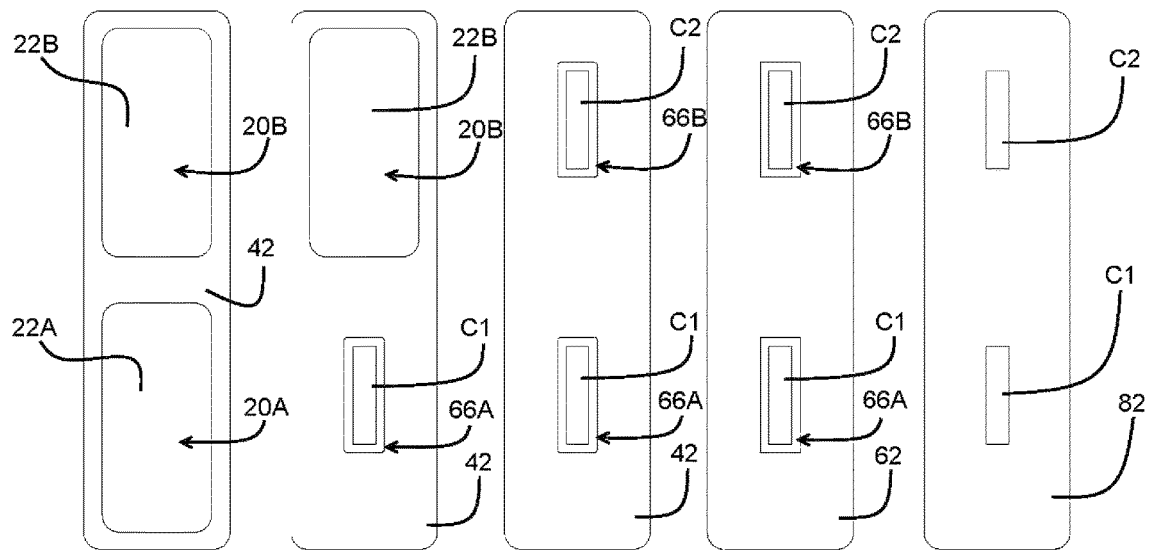
FIG. 2D is a layer-by-layer process view of the functional package of FIGS. 2A-2C.
Figure 2E:
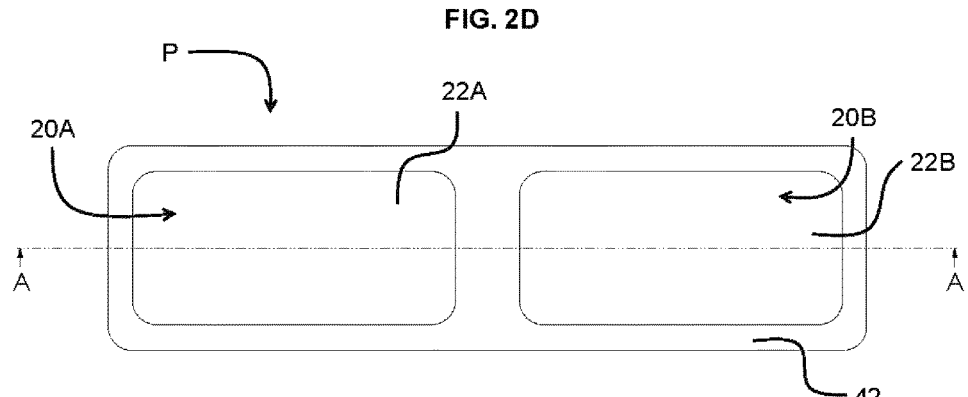
FIG. 2E is a top view of the functional package of FIGS. 2A-2C, showing location of cross section A-A.
Figure 2F:
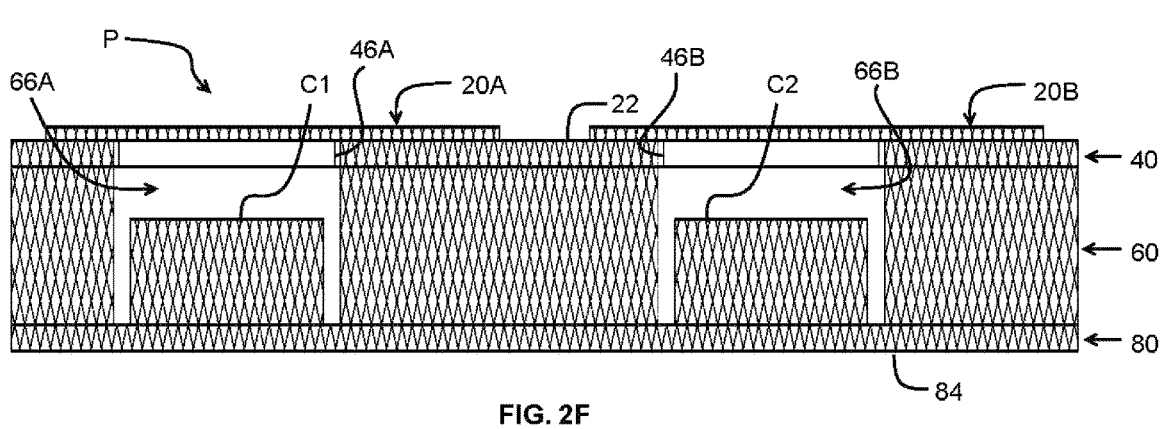
FIG. 2F is a cross-sectional view A-A of FIG. 2E.

FIG. 2D shows an example of a layer-by-layer process of producing the laminate design of package P to house contents C1, C2, sequenced generally from right to left, and which may also be understood with reference to FIG. 2C sequenced generally from bottom to top. However, as described previously with reference to FIG. 1D, these are simply non-limiting examples, and as may be appreciated by someone skilled in the art of roll-to-roll manufacturing, the order and method of processing, printing and laminating separate web-based materials is highly flexible and customizable and dependent on machine design, speed and productivity requirements, cost and other factors.

Figure 3D:
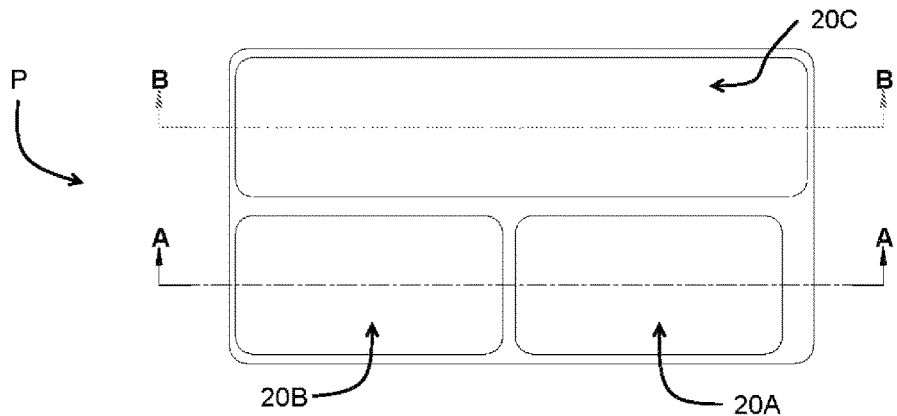
FIG. 3D is a top view of the functional package of FIGS. 3A-3C, showing location of cross sections A-A and B-B.

FIGS. 3A and 3B are isometric views of another example package P according to the present disclosure, and FIG. 3C is an isometric exploded view. The package P design of FIGS. 3A-3F builds upon the design of the package described with reference to FIGS. 2A-2F, adding a third label 20C having top surface 22C and bottom surface 24C, third opening 46C, third void 66C and third package content C3, such as configured for an in-vitro diagnostic device, including but not limited to an LFA.

First label 20A, second label 20B, and additional third label 20C are provided to cover each opening 46A, 46B, 46C, respectively, in top layer 40, and each may be sequentially peeled away or otherwise removed from the top layer 40 as shown in FIG. 3B with respect to third label 20C. Each opening 46A, 46B and 46C is in communication with first void 66A, second void 66B, and third void 66C, respectively, disposed in the same intermediate layer 60. As described previously, kiss cut material 26 may likewise be utilized to form one or more of openings 46A, 46B and 46C when labels 20A, 20B, and 20C are peeled away. Further, each of the first void 66A, second void 66B, and third void 66C may independently house a first package content C1, a second package content C2 and third package content C3, as shown. Each package content C1, C2, C3 may be different, or may be redundant depending on the particular functionality desired for package P.

Figure 3E:
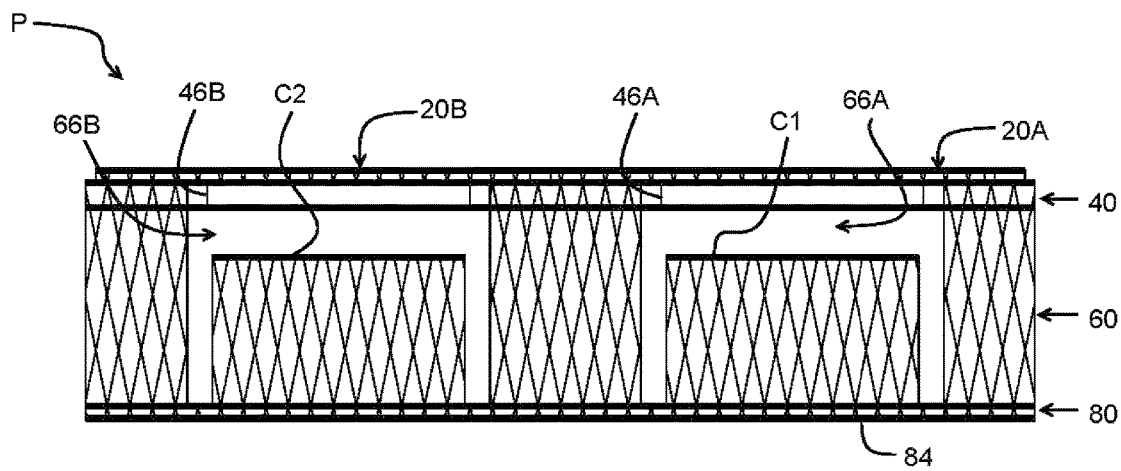
FIG. 3E is a cross-sectional view A-A of FIG. 3D.
Figure 3F:
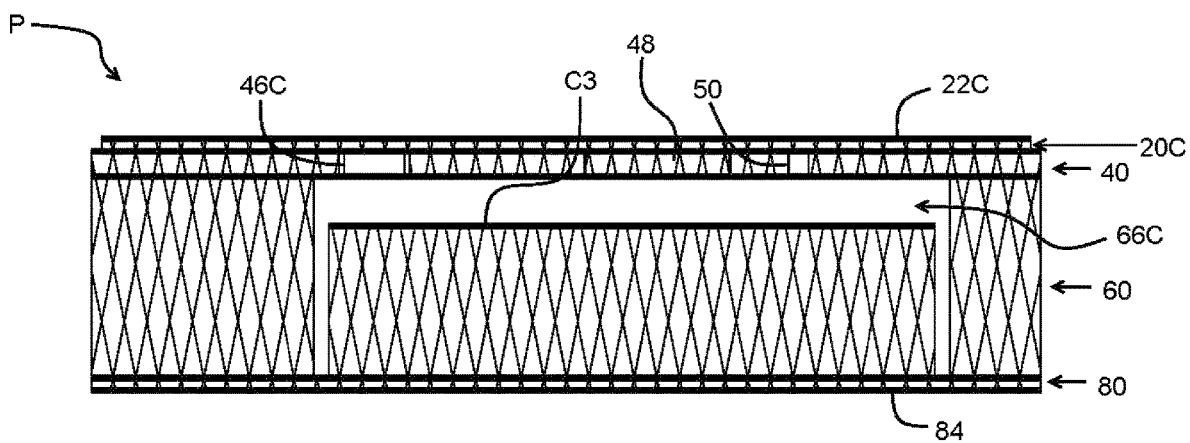
FIG. 3F is a cross-sectional view B-B of FIG. 3D.

Communication between the each void 66A, 66B and 66C and the external environment is provided via their respective openings 46A, 46B, and 46C, as further shown in the detail of the cross-sectional views of FIGS. 3E and 3F, which represent cross sections A-A and B-B, respectively, of the package P shown in FIG. 3D (showing a top view of the package P). As described previously, openings 46A, 46B, and 46C may be sized appropriately depending on the desired function in relation to each package contents C1, C2, and C3. Accordingly, package P of FIGS. 3A-3F may provide for a multi-component diagnostic test kit, and printed information on the top surface 62 of each label 20A, 20B, 20C may instruct or otherwise guide the user, including for example the sequence in which to perform the steps of the diagnostic test, among other useful information.

Although three functional voids 66A, 66B, 66C are shown in this example, any number of voids in intermediate layer 60 may be envisioned according to the number of package contents and desired functionality of the package P. Further, it may be understood that not all openings 46A, 46B, 46C need to be formed by a kiss cut method, and some may simply comprise a through-hole covered by a label where such structure is beneficial or satisfactory in relation to package contents, function, and environmental barrier specifications, among other considerations.

As described previously, a process of producing the laminate design of package P to house contents C1, C2, C3 may be appreciated in the art, and enabled by the layered, web-based construction of the present disclosure.

Figure 4C:
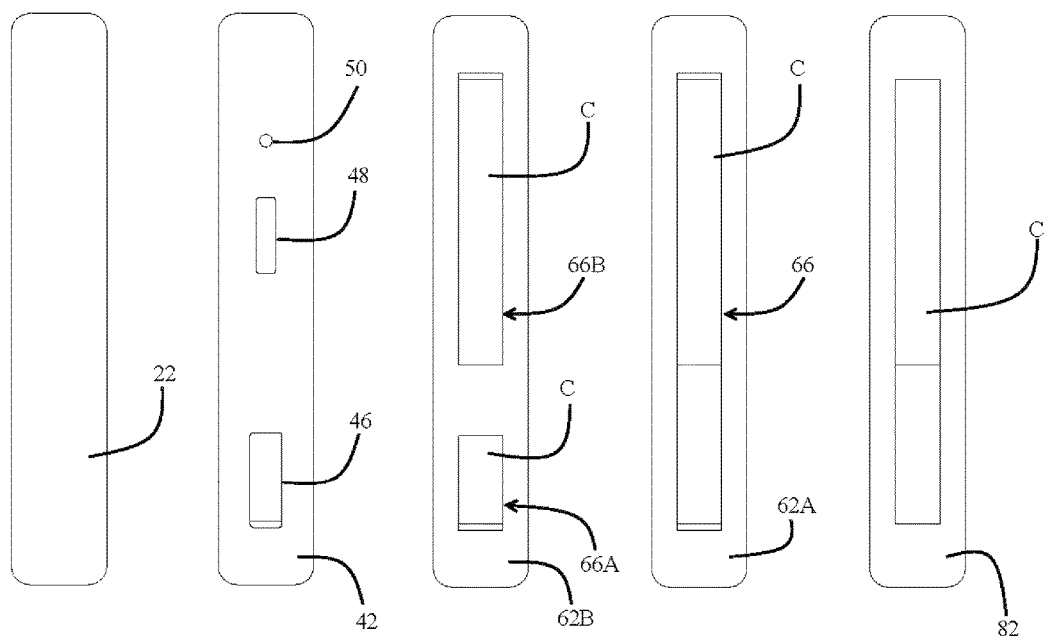
FIG. 4C is a layer-by-layer process view of the functional package of FIGS. 4A and 4B.
Figure 4D:
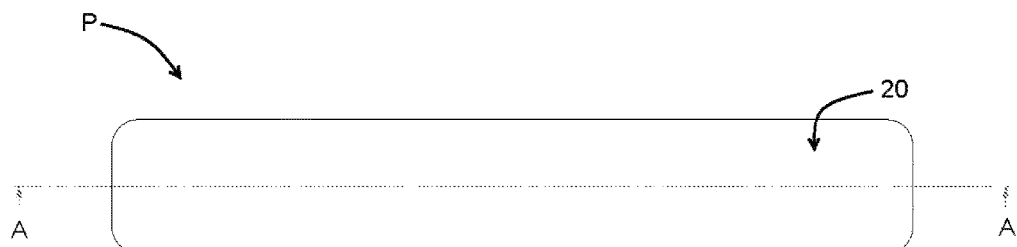
FIG. 4D is a top view of the functional package of FIGS. 4A-4C, showing the location of cross section A-A.
Figure 4E:
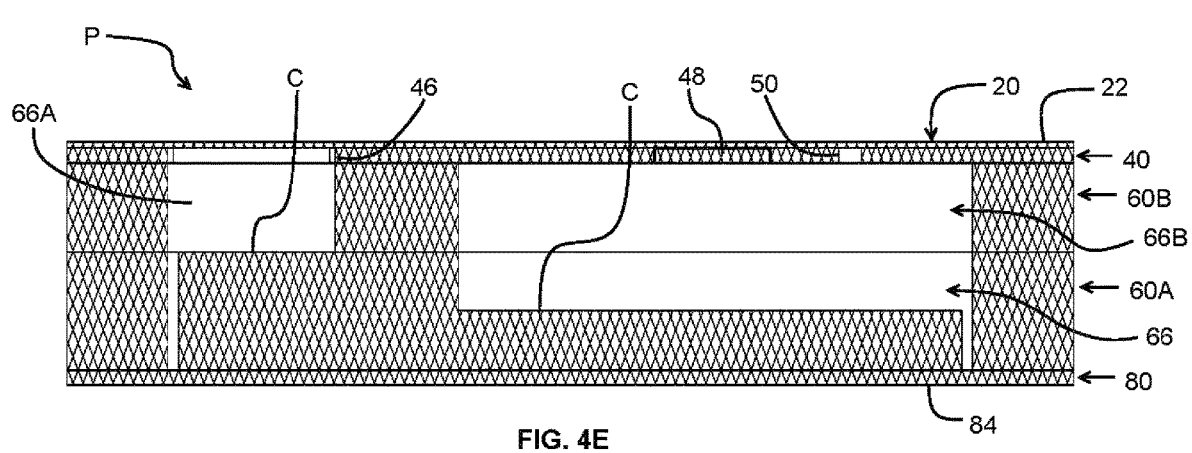
FIG. 4E is a cross-sectional view A-A of FIG. 4D.

FIG. 4A is an isometric view of another example package P according to the present disclosure, with label 20 partially peeled back to expose the features on top layer 40, and FIG. 4B is an isometric exploded view of FIG. 4A. The package P design of FIGS. 4A-4E provides a second intermediate layer 60B in addition to a first intermediate layer 60A (or intermediate layer 60 as described previously) disposed between the top layer 40 and bottom layer 80, the first intermediate layer having a top surface 62A and bottom surface 64A, and the second intermediate layer 60B having a top surface 62B and bottom surface 64B. Where a package content C comprises an irregular or uneven surface topology, protrusions or other prominent features, such as shown in the views of FIGS. 4B and 4E, a second intermediate layer 60B may be utilized comprising a first void 66A and second void 66B configured to accommodate such features, each of the first and second voids in communication with void 66 in the first intermediate layer 60A. Alternatively, any number of intermediate layers 60 may be disposed between the top layer 40 and bottom layer 80 of the package, each with one or more voids 66 spatially related and configured to accommodate the unique features of the packaged content.

As described previously, label 20 is provided to cover an opening 46, and in the present example, is shown in communication with first void 66A in second intermediate layer 60B, which in turn is in communication with void 66 of the first intermediate layer 60A. In the example of FIGS. 4A-4E, window 48 is aligned over the second void 66B in the second intermediate layer 60B, which in turn is in communication with void 66 in first intermediate layer 60A as well as an assay result display portion of package content C, for example. This may also be appreciated from the diagram of FIG. 4E, which is a cross-sectional view A-A of the package shown in FIG. 4D (showing a top view of package P). First void 66A may be configured, for example, such that it makes contact with a top surface of package content C1, such as an LFA, to isolate a portion of the content C1, such as a sample receiving portion. In the present embodiment, first void 66A with opening 46 could be dipped into a biological sample, such as blood, saliva or urine, and then the results of the assay performed by the packaged content C1 could be viewed through window 48 which is aligned over second void 66B and void 66. This is facilitated by the configured horizontal and vertical arrangements of the first void 66A, second void 66B, and void 66 in intermediate layers 60A and 60B.

FIG. 4C shows an example of a layer-by-layer process of producing the laminate design of package P to house content C, sequenced generally from right to left, and which may also be understood with reference to FIG. 4B sequenced generally from bottom to top. However, as described previously, a process of producing the laminate design of package P including content C may be appreciated in the art, and is flexibly enabled by the layered, web-based construction of the present disclosure.

Figure 5A:
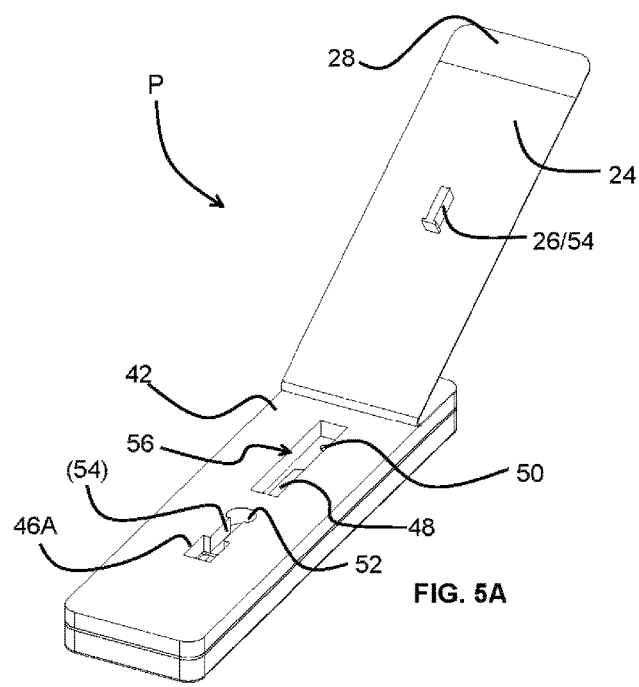
FIG. 5A is an isometric view of a functional package according to the present disclosure, showing a label peeled back.
Figure 5B:
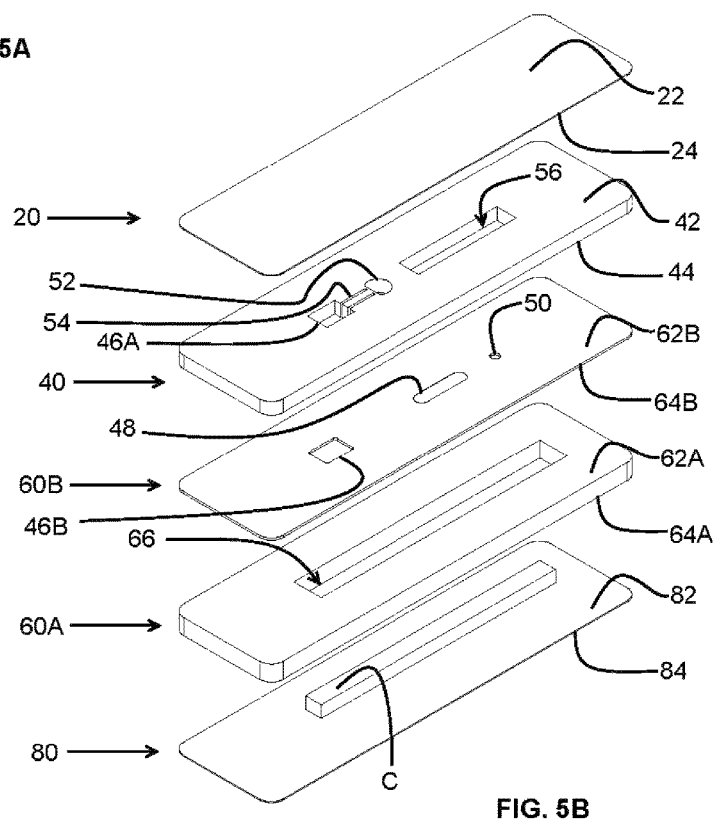
FIG. 5B is an isometric exploded view of the layers of the functional package of FIG. 5A.

FIG. 5A is an isometric view of another example package P according to the present disclosure, with label 20 partially peeled back to expose the features on top layer 40, and FIG. 5B is an isometric exploded view of FIG. 5A. The package P design of FIGS. 5A-5E provide a second intermediate layer 60B in addition to a first intermediate layer 60A (or intermediate layer 60 as described previously) disposed between the top layer 40 and bottom layer 80. However, in the present example, second intermediate layer 60B may comprise some features previously shown for top layer 40 in previous examples, and top layer 40 may comprise some features previously shown for an intermediate layer 60 in previous examples. In this example, top layer 40 comprises a reservoir 52, a gate 54 (e.g., kiss-cut material), and a void 56. Underneath top layer 40 is second intermediate layer 60B, which acts as a barrier between reservoir 52 and void 66 in the first intermediate layer 60A. This may also be appreciated with reference to FIG. 5E, which is a cross section A-A of FIG. 5D (showing a top view of package P). When the label 20 is removed, gate 54 (kiss cut material 26) is pulled away, thereby removing the gate 54 from top layer 40 to create empty gate (54) in the top layer, and allowing any fluid contents of reservoir 52 to flow into opening 46A in top layer 40. In other words, establishing fluid communication between reservoir 52 and opening 46A. Opening 46A is aligned with opening 46B in second intermediate layer 60B below it, which in turn is in communication with void 66 in first intermediate layer 60A below that. Accordingly, the removal of kiss cut gate 54 allows any fluid to flow freely from reservoir 52 into void 66 in first intermediate layer 60A, and to come into contact with packaged content C inside that void. In the case of an in-vitro diagnostic tests such as an LFA, void 56 in top layer 40 is provided in communication with window 48 in second intermediate layer 60B, and is further positioned over any assay result portion of the LFA packaged content C below it within void 66. Void 56 in top layer 40 may also be in contact with vent 50 provided in second intermediate layer 60B to serve the function described previously.

Accordingly, the example packager P of FIGS. 5A-5E may provide another mechanism for user-friendly diagnostic testing, particularly where a reagent is required to be kept isolated until the time of use, and subsequently mixed with a biological sample for analysis via a diagnostic test device, such as an LFA. This self-inclusive functional package design can therefore eliminate the need to provide a separate sealed vial or other container containing a fluid reagent, and can also eliminate the necessity of using a pipette, dropper, or other tool to dispense that reagent.

Figure 5C:
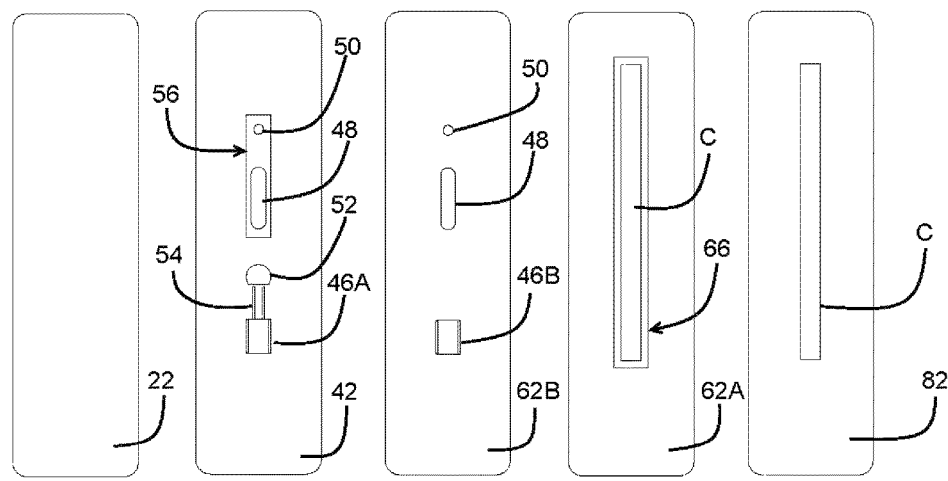
FIG. 5C is a layer-by-layer process view of the functional package of FIGS. 5A and 5B.
Figure 5D:
FIG. 5D is a top view of the functional package of FIGS. 5A-5C, showing the location of cross section A-A.
Figure 5E:
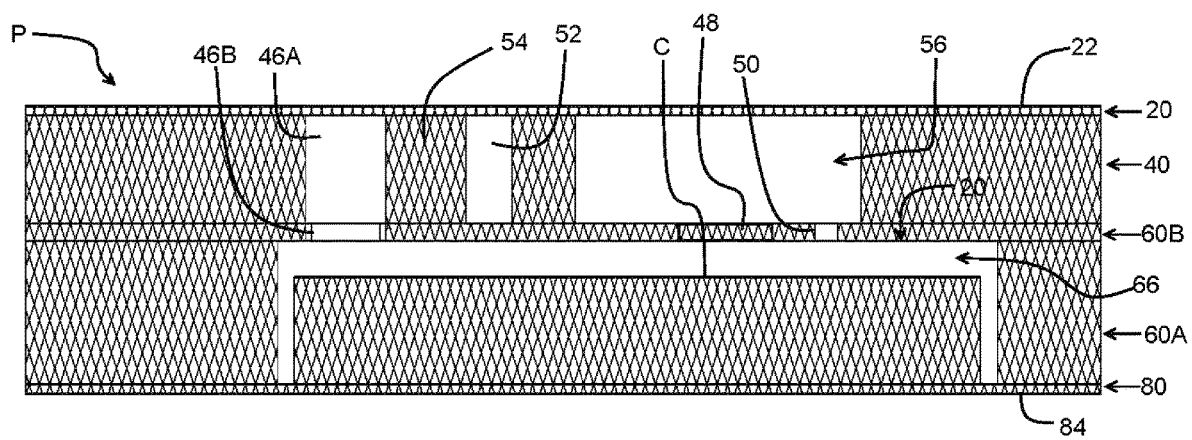
FIG. 5E is a cross-sectional view A-A of FIG. 5D.

FIG. 5C shows an example of a layer-by-layer process of producing the laminate design of package P to house content C, sequenced generally from right to left, and which may also be understood with reference to FIG. 5B sequenced generally from bottom to top. However, as described previously, a process of producing the laminate design of package P including content C may be appreciated in the art, and is flexibly enabled by the layered, web-based construction of the present disclosure.

Figure 6A:
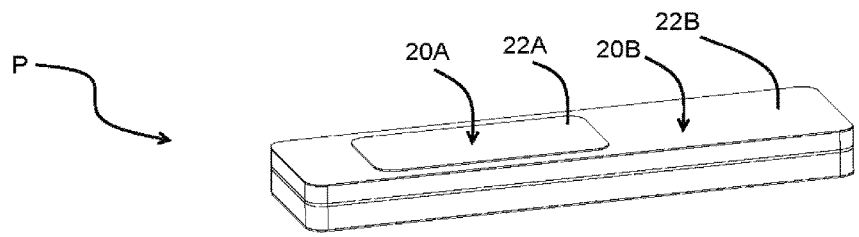
FIG. 6A is an isometric view of a functional package according to the present disclosure.
Figure 6B:
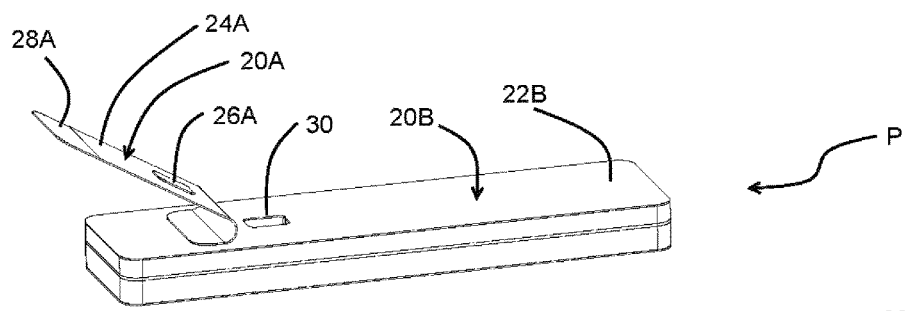
FIG. 6B is an isometric view of the functional package of FIG. 6A, showing a first label peeled back.
Figure 6D:
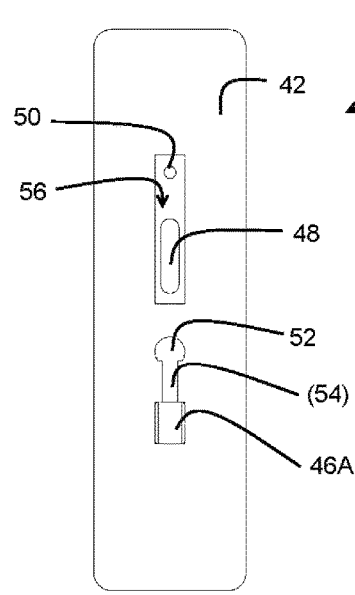
FIG. 6D is a top view of the functional package of FIGS. 6A-6C with all labels removed.
Figure 6C:
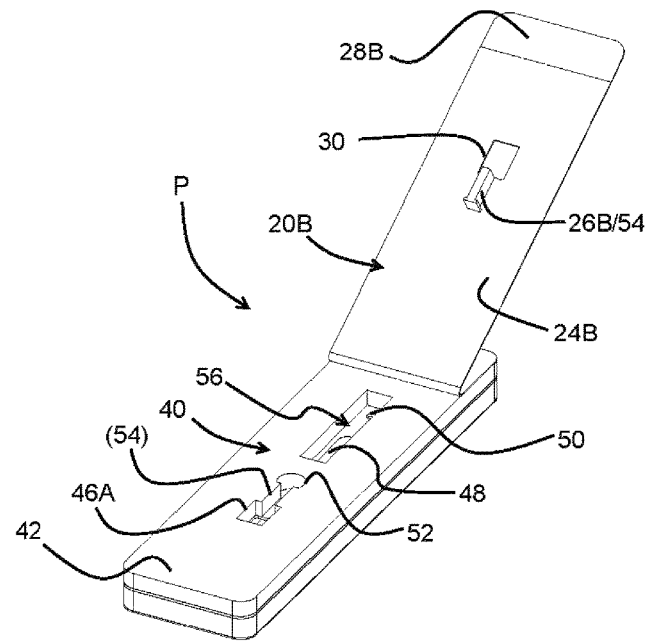
FIG. 6C is an isometric view of the functional package of FIGS. 6A and 6B, showing a second label peeled back.
Figure 6E:
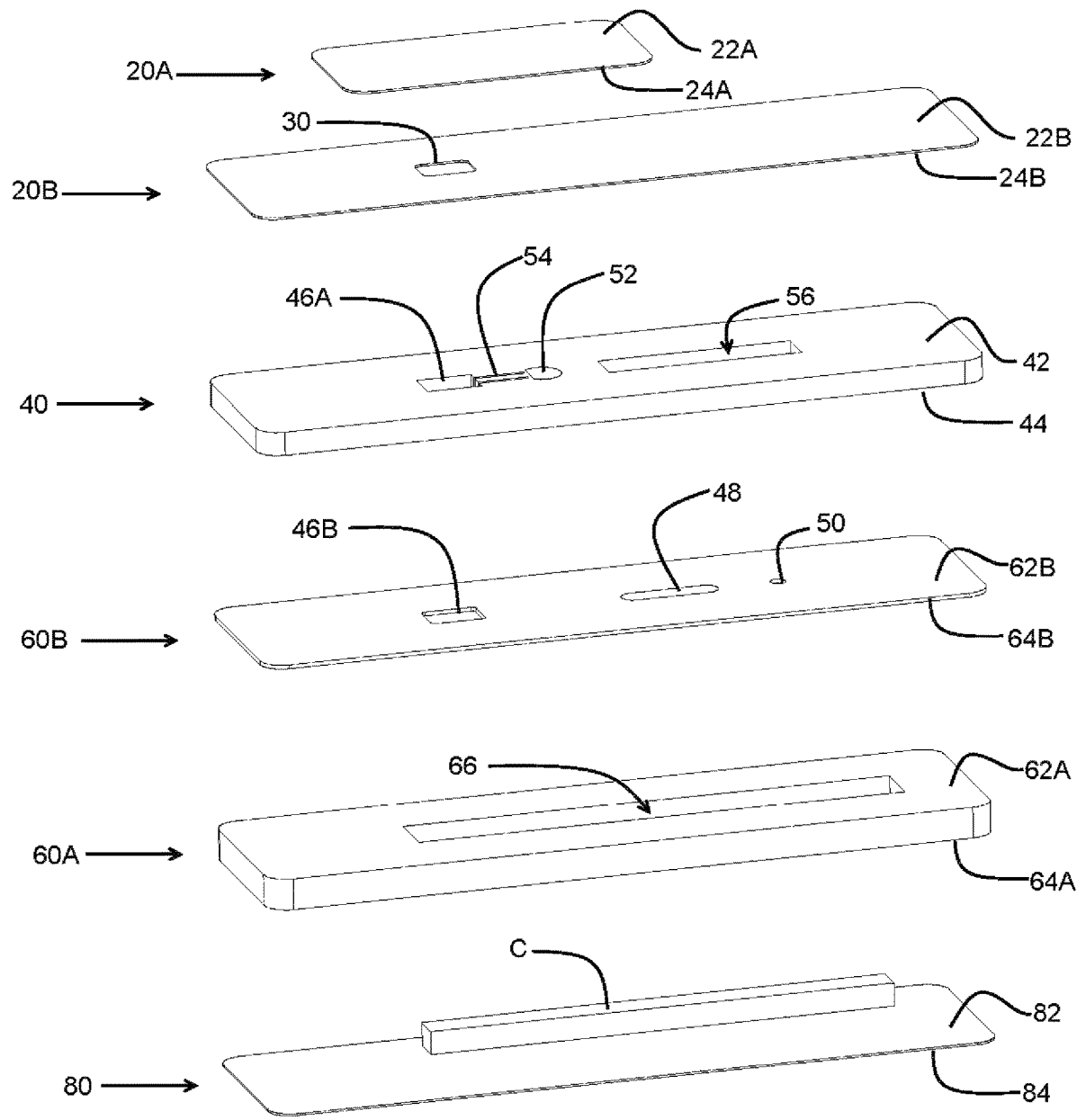
FIG. 6E is an isometric exploded view of the layers of the functional package of FIGS. 6A-6D.
Figure 6F:
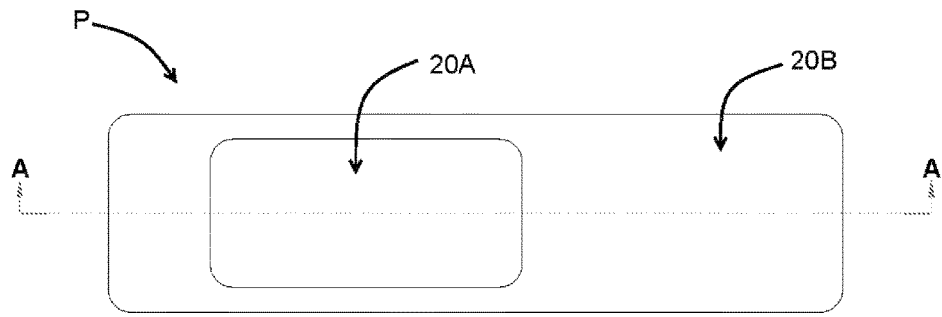
FIG. 6F is a top view of the functional package of FIGS. 6A-6D, showing the location of cross section A-A.
Figure 6G:
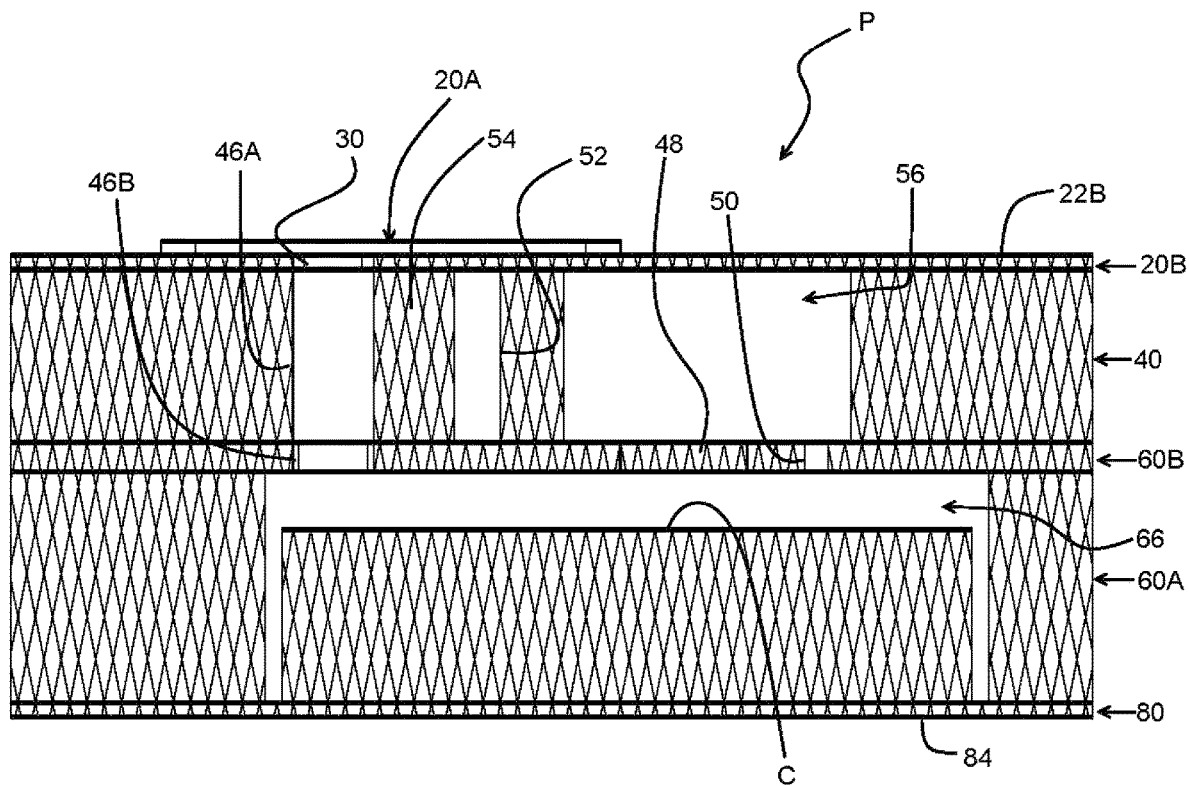
FIG. 6G is a cross-sectional view A-A of FIG. 6F.

FIGS. 6A-6C are isometric views of another example package P according to the present disclosure, FIG. 6E is an exploded isometric view of the same, and FIG. 6G is a cross section A-A of FIG. 6F (showing a top view of package P). As shown in the example of these Figures, a first label 20A is affixed to the top surface of a second label 20B, which is in turn affixed to the top layer 40 of the package P. An example sequence of label removal is shown, with FIG. 6A representing the unopened package P, FIG. 6B showing first label 20A removed including removal of kiss cut material 26A on bottom surface 24A to expose label opening 30 in second label 20B; FIG. 6C showing second label 20B peeled back to remove gate 54 (kiss cut material 26B/54 on bottom surface 24B) that was adjacent reservoir 52, leaving empty gate (54) and exposing the features on top layer 40. When gate 54 is removed from top layer 40, it places reservoir 52 in communication with opening 46A as shown. FIG. 6D is a top view of package P with both labels 20A, 20B removed, showing the view a user would see after having removed both labels 20A and 20B.

Although similar structures and functions are disclosed as was described with reference to FIGS. 5A-5E, including for example features of the top layer 40, first intermediate layer 60A and second intermediate layer 60B, the present example utilizing two labels 20A and 20B adds further useful functionality to package P. For example, removal of first label 20A including kiss cut material 26 exposes label opening 30, which is aligned with and in communication with opening 46A below it. Accordingly, first label 20A allows opening 46A to be accessed without opening gate 54 between opening 46A and reservoir 52. In case of an in-vitro diagnostic test kit, for example, a sample specimen may be placed using a tool (e.g., via swab, pipette, or other know methods) onto package content C through opening 46A (which in turn opens to 46B and void 66 with product C, all in fluid communication with one another), as a first step in an assay. Then, after a period of time to allow the sample to mix, stabilize or react with package content C if necessary, second label 20B may be removed to open gate 54 and allow the reagent to flow from reservoir 52 into first opening 46A, second opening 46B, and subsequently into void 66 of the first intermediate layer 60A and come into contact with package content C, such as an LFA, according to the method and structures previously described with reference to FIGS. 5A-5E. In this manner, a reagent can be stored separately from the sample and package content C and released as a step of the assay utilizing the functional package design. In the case of an in-vitro diagnostic tests such as an LFA, void 56 in top layer 40 is provided in communication with window 48 in second intermediate layer 60B, and is further positioned over any assay result portion of the LFA packaged content C below it within void 66. Void 56 in top layer 40 may also be in contact with vent 50 provided in second intermediate layer 60B to serve the function described previously.

As previously described, any suitable layer-by-layer process may be utilized to produce the laminate design of package P to house content C, which may be understood with reference to FIG. 6E sequenced generally from bottom to top. However, as described previously, a process of producing the laminate design of package P including content C may be appreciated in the art, and is flexibly enabled by the layered, web-based construction of the present disclosure.

Figure 7A:
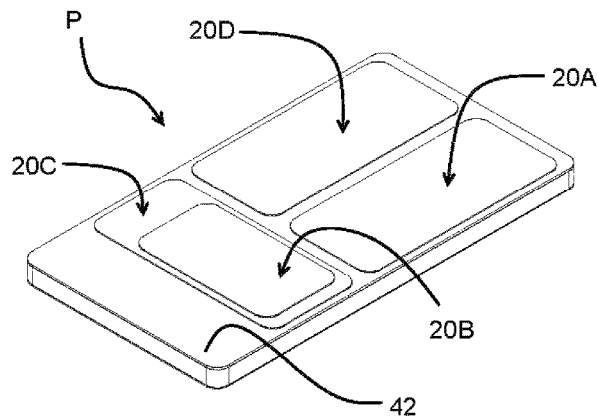
FIG. 7A is an isometric view of a functional package according to the present disclosure.
Figure 7B:
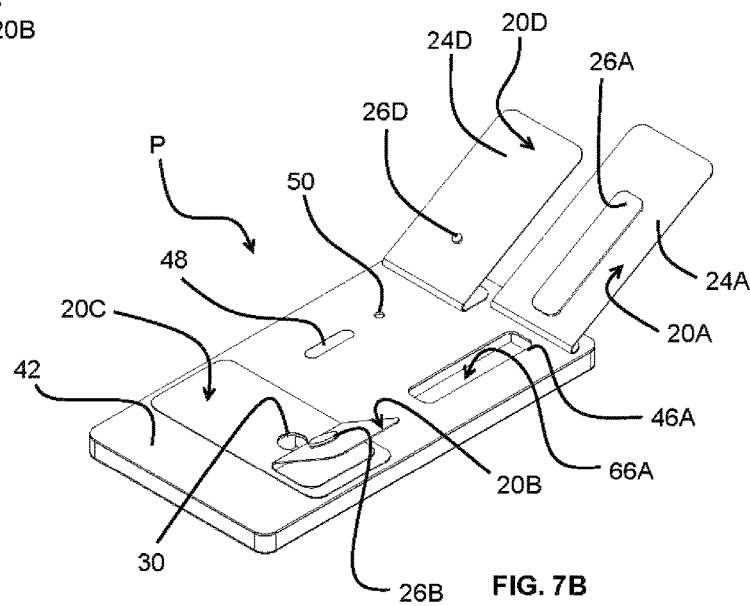
FIG. 7B is an isometric view of the functional package of FIG. 7A, showing three labels peeled back.
Figure 7C:
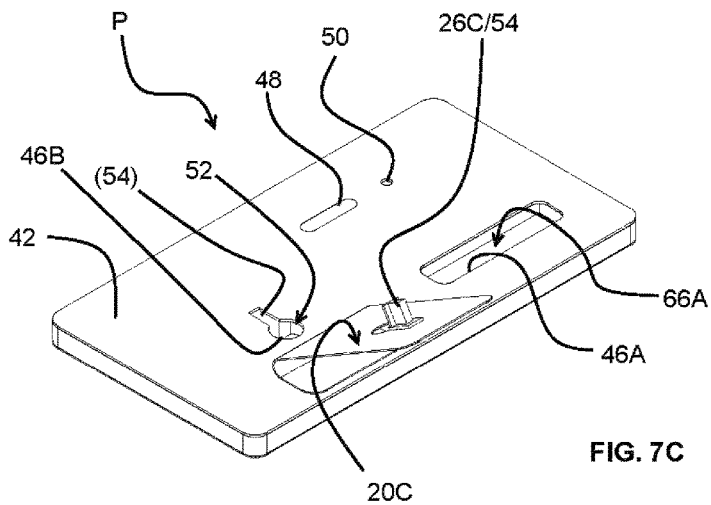
FIG. 7C is an isometric view of the functional package of FIGS. 7A and 7B, showing a fourth label peeled back.

FIGS. 7A-7C are isometric views of another example package P according to the present disclosure, representing an example of a more complex, multi-component and multi-step in vitro diagnostic test that is enabled by the inventive technology of the laminate package P design and combination of some of the various features and functions described previously. An exploded isometric view of package P is also provided in FIG. 7D, and a top view of the package showing internal hidden features is shown with reference to FIG. 7E.

As may be appreciated from FIGS. 7A-7E, package P may be utilized and function according to the following example sequence. First label 20A is removed from top layer 40 to expose a first opening 46A in communication with a first void 66A in intermediate layer 60, such as to provide access to a first package content C1, such as a sample collection tool (e.g., finger-prick needle or lancet, nasal or throat swab, etc). Next, second label 20B is removed from third label 20C to expose label opening 30 in third label 20C which is aligned with second opening 46B in top layer 40 and reservoir 52 below it disposed in intermediate layer 60. A sample specimen is collected and placed through opening 30 to come into contact with fluid or reagent in reservoir 52. After a period of time to allow sufficient mixture, reaction or stabilization of the specimen in the reagent, third label 20C is peeled away, pulling out gate 54 (kiss cut material 26C) to create open gate (54), and allowing the sample-reagent fluid mixture to flow laterally from reservoir 52 through a channel 58 into second void 66B and in contact with package content C2, which may comprise a in-vitro diagnostic test device such as an LFA. Lastly, fourth label 20D is removed from top layer 40 to expose the window 48 for viewing the result of the diagnostic test, as well as the optional vent 50 to function as described previously. As an example, the reagent may include a suspension buffer for facilitating extraction of the biological sample, such as DNA from a swab, and/or stabilizing it for purposes of the subsequent assay by package content C.

According to this example, a highly functional package design is provided to facilitate a multi-component, step-by-step assay in a completely self-inclusive design. Further, as described previously, the web-based materials of each label and layer provide a large and easily printable surface area such that clear instructions may be provided on the surface of the package P to guide the user in accurately performing the assay, including but not limited to numbering, lettering or otherwise coding each label and step. Further, as shown, the flow of reagents or fluids can be accomplished laterally within the same layer (here intermediate layer 60), in addition to vertically between multiple layers as described with reference to previous examples.

Figure 7D:
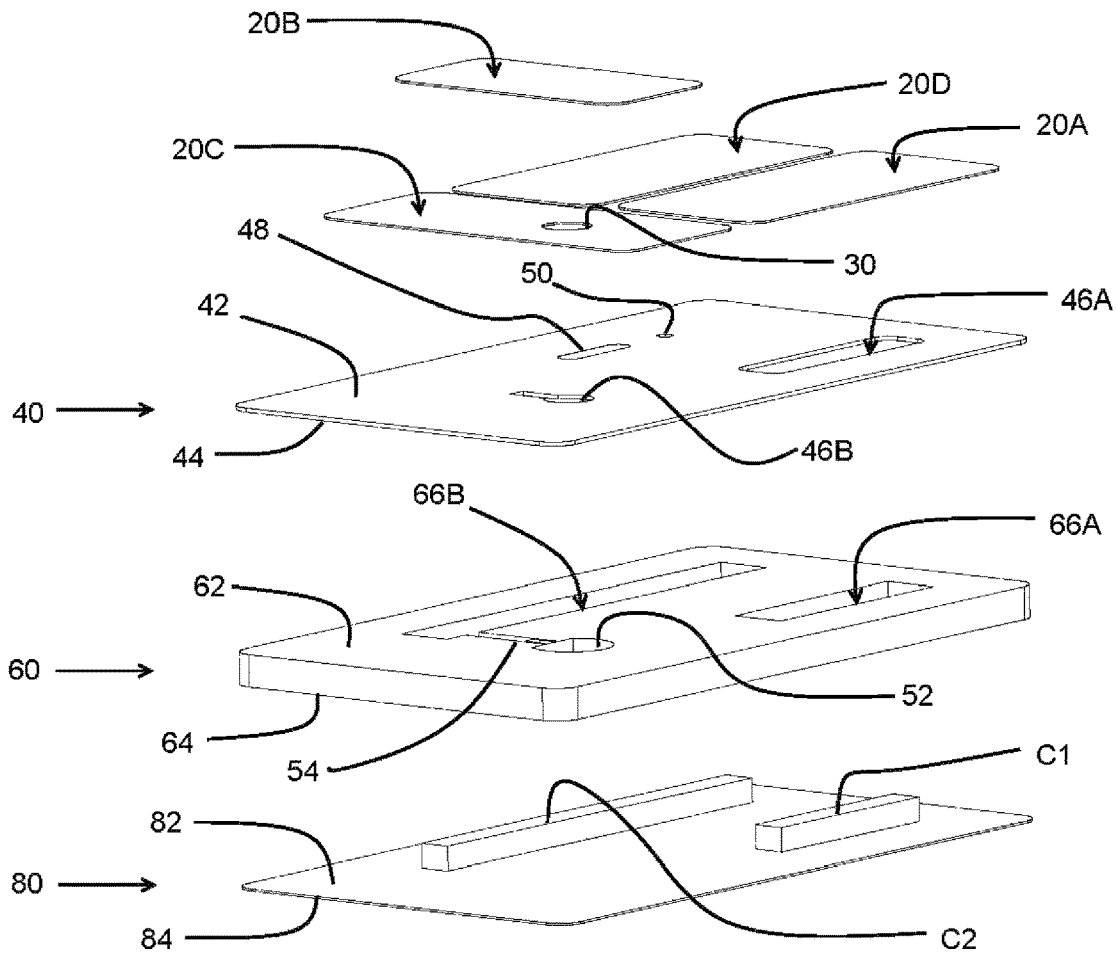
FIG. 7D is an isometric exploded view of the layers of the functional package of FIGS. 7A-7C.
Figure 7E:
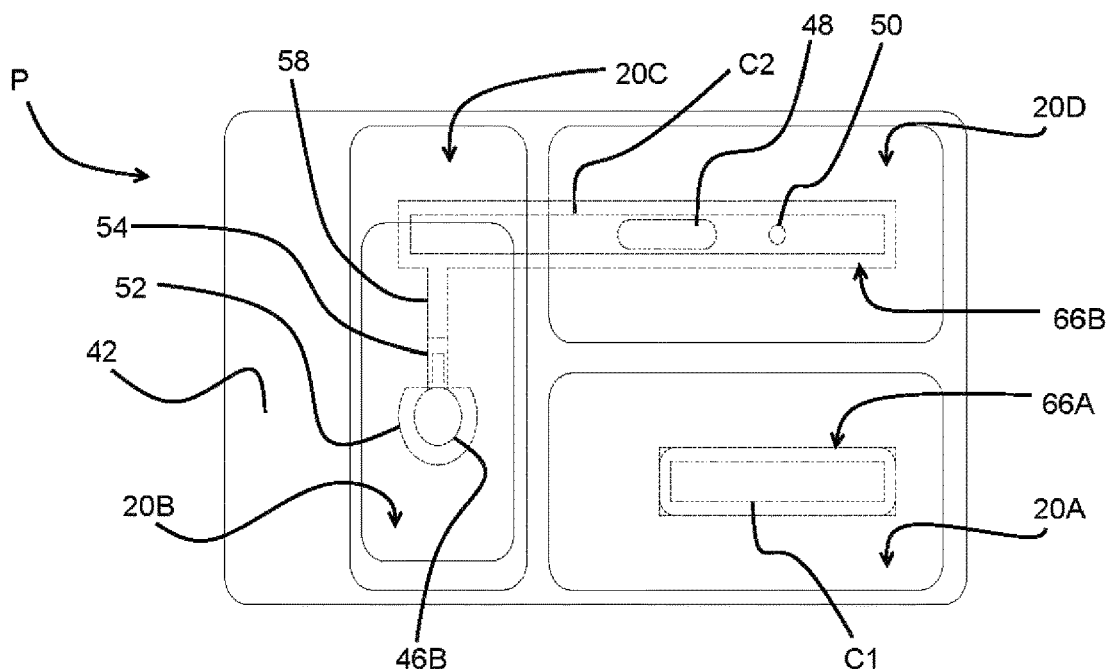
FIG. 7E is a top view of the functional package of FIGS. 7A-7D, showing hidden internal features beneath the top surface of the package.

As previously described, any suitable layer-by-layer process may be utilized to produce the laminate design of package P to house content C1 and C2, including material in reservoir 52, which may be understood with reference to FIG. 7D sequenced generally from bottom to top. However, as described previously, a process of producing the laminate design of package P including content C1 and C2 may be appreciated in the art, and is flexibly enabled by the layered, web-based construction of the present disclosure.

Figure 8A:
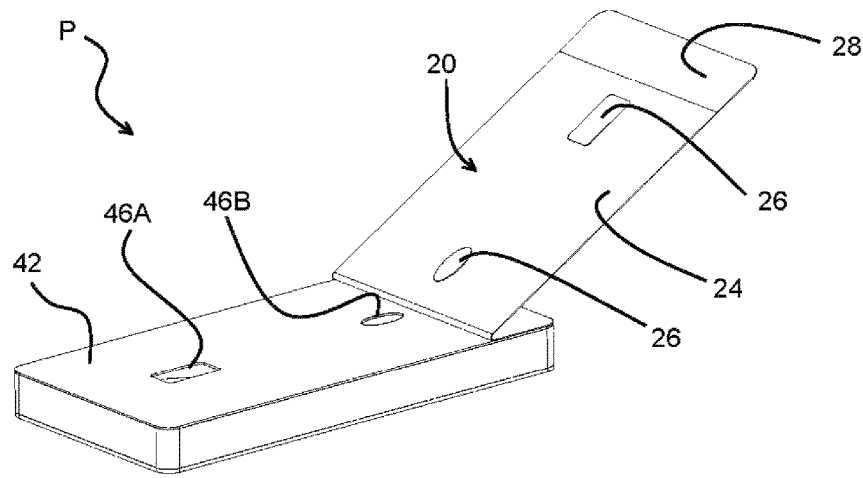
FIG. 8A is an isometric view of a functional package according to the present disclosure, showing a label peeled back.
Figure 8B:
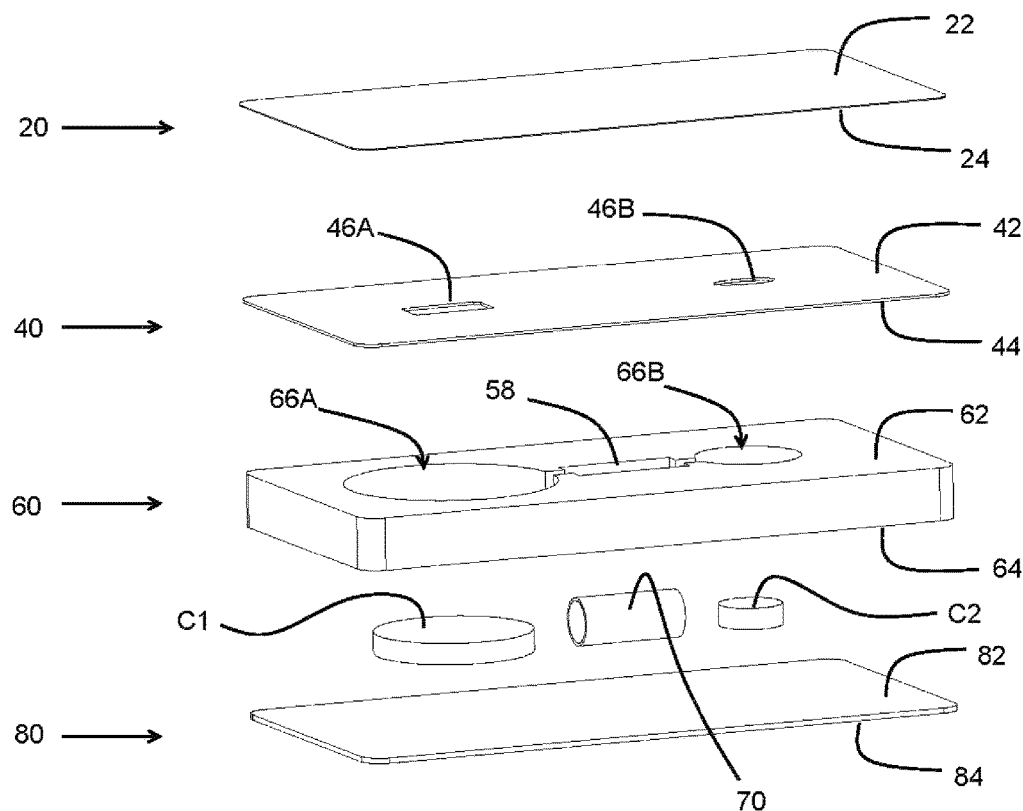
FIG. 8B is an isometric exploded view of the functional package of FIG. 8A.

FIG. 8A is an isometric view of another example of package P, with an isometric exploded view provided in FIG. 8B. In this example, package P includes a breakable vial 70 disposed in intermediate layer 60 in channel 58 which is in fluid communication with voids 66A, 66B containing package contents C1, C2, respectively. Because the laminate structure of package P can be produced to maintain a requisite degree of rigidity while also imparting some flexibility to the package, package P may be bent near the middle where breakable vial 70 is positioned, or otherwise pinched or compressed at that position, thereby breaking vial 70 and allowing its contents to flow into the one or more adjacent voids 66A, 66B to interact with contents C1, C2. Such mechanism may be beneficial where a reagent or chemical substance requires separate, isolated storage until end-use, similar to the concept of the reservoir 52 and gate 54 mechanism described previously. However, utilizing a vial may in some cases be beneficial when storing a reagent or substance that is not chemically compatible or shelf-stable with the web-based materials used to construct package P, such as foam, plastics, etc, but is compatible with the material of the vial, such as glass or crystal. Further, crushing the glass or crystal in some cases may be a more reliable or simpler user operation depending on the intended function of the package P.

Additionally, it may be appreciated that the labels may be configured to be resealable with the appropriate selection of adhesive, thus allowing the user to safely contain any potentially hazardous biological sample or reagent within the package. This enables the safe disposal of the hazardous contents with the functional package, as well as the ability to securely store a biological sample for mailing to a remote laboratory, for example, for DNA testing or other analyses. Examples of suitable resealable labels can be found, for example, in U.S. Pat. Nos. 10,155,614 "Peel Reclose Package with Laser Features," and 9,422,080 "Process to Manufacture Peel-Reclose Packaging Film Using Laser Scoring and Pressure Sensitive Labels," both by Tinoco et al. and assigned to LaserSharp FlexPak Services, LLC.

Further, any of the labels 20 of package P may comprise a tamper-resistant or tamper-evident feature to provide extra security for the package and its contents C. Examples of suitable tamper-resistant or tamper-evident features can be found, for example, in U.S. Pat. No. 10,214,335 "Tamper Evidence Feature" by Tinoco and assigned to LaserSharp FlexPak Services, LLC, as well as U.S. Design Pat. No. 811,871 "Tamper Evident Package with Spiral Feature" by Tinoco and assigned to LaserSharp FlexPak Services, LLC.

Although the geometry of each package P shown and described with reference to the Figures of the present disclosure are generally rectangular in shape, the invention described herein is not limited to any particular geometry, and other shapes and designs are envisioned, including circular or oblong, triangular, and more complex patterns compatible with roll-to-roll manufacturing techniques.

Further, although the examples of each package P shown and described with reference to the Figures of the present disclosure included at least a top layer, intermediate layer, and bottom layer, it is envisioned that the package P may also be formed with only two layers, for example, where one of the layers may comprise foam having a void cut out to a defined depth that does not penetrate through the entire layer, and the other layer is laminated to cover the void of the foam layer. In such case, the bottom layer and one or more intermediate layers of the previous examples may be combined into a single foam layer.

Further, due to the sealable nature of package P disclosed herein and the ability to select for environmental barrier materials, the internal environment of package P may be modified or controlled by providing a desiccant, humectant, or other atmosphere modifying compound, for example, in a void 66 of the package or as another package content C.

The examples of the present disclosure enable and teach a highly advantageous functional package design compatible with a wide spectrum of end uses in the medical and life sciences industries, including diagnostic assays, in-vitro test kits and many others. By designing all elements of the package to be compatible with high-speed roll-to-roll manufacturing techniques, the package may be produced at much faster rates than any injected molded cassette used for common in-vitro diagnostics such as LFAs.

Further, where the package contents are also produced with roll-to-roll or other high-speed manufacturing processes, the package design of the present disclosure enables the in-line integration of the package production process with the package content production process. In case of a packaged LFA, the package designs disclosed herein may be introduced downstream and in-line with the roll-to-roll LFA production, resulting in a much more efficient manufacturing process and smaller footprint for production equipment compared with traditional hard molded cassette designs. With respect to solid or liquid contents placed within the package designs of the present disclosure, any high-speed placement mechanisms compatible with roll-to-roll manufacturing equipment may be advantageously utilized as is known by those skilled in the art. The printing of instructions, warnings or other useful or necessary information on the package P and labels of the present disclosure may be accomplished in-line with the high speed roll-to-roll manufacturing process using flexographic printing techniques, in contrast with inkjet or other slower printing methods typically required for printing molded plastic housings.

Further, due to the completely self-inclusive nature of the functional package design, over-packaging waste and the need for separate storage vessels and implements for multi-component test kits may be significantly reduced or eliminated. Due to the large, printable surface area and use of removable labels, the package design disclosed herein enables the effective use of information on the package itself to clearly instruct a user how to perform sequential multi-step assays with no need for a separate instruction booklet or materials. These and many other advantages are apparent with reference to the disclosure and figures provided herein.

While the invention has been described with reference to exemplary embodiment(s), it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A functional laminate package comprising:
    a bottom layer;
    a top layer comprising an opening;
    an intermediate layer disposed between the bottom layer and the top layer, and comprising a void configured to house a package content and in communication with the opening in the top layer; and
    a removable label affixed to the top layer covering the opening, wherein the opening is kiss cut through the top layer against a bottom surface of the removable label, such that when the label is removed, kiss cut material from the top layer is removed with the label to form the opening in the top layer.

2. The functional laminate package of claim 1, further comprising a reservoir adjacent the opening and a gate therebetween, wherein the gate is configured to be removed with the label to establish a flow path between the reservoir and the opening.

3. The functional laminate package of claim 1, further comprising a plurality of removable labels, each covering an independent void in the intermediate layer and configured to house separate package contents.

4. The functional laminate package of claim 1, further comprising a plurality of voids in the intermediate layer, and wherein at least two of the voids are in lateral fluid communication.

5. The functional laminate package of claim 1, further comprising a plurality of intermediate layers, each layer comprising a void, and wherein the void from one intermediate layer is in fluid communication with the void from another intermediate layer.

6. The functional laminate package of claim 1, further comprising an in-vitro diagnostic test or assay within the void.

7. The functional laminate package of claim 6, wherein the in-vitro diagnostic test or assay is a lateral flow assay.

8. The functional laminate package of claim 1, further comprising a sample collection tool, a reagent, or a breakable vial within the void.

9. The functional laminate package of claim 1, further comprising a second label affixed to the removable label, wherein both the removable label and the top layer comprise a kiss cut opening against the bottom of the second label.

10. The functional laminate package of claim 1, wherein the intermediate layer comprises a roll-based foam.

11. The functional laminate package of claim 1, wherein either the top or bottom layer comprises a web-based polymer material.

12. The functional laminate package of claim 1, wherein a top surface of the bottom layer comprises an adhesive layer for affixing to the package content.

13. The functional laminate package of claim 1, wherein the top layer comprises a window in communication with the void in the intermediate layer.

14. The functional laminate package of claim 1, further comprising printed information on the label instructing the user how to utilize the functional package.

15. A functional laminate package comprising:
a bottom layer;
a top layer comprising an opening;
an intermediate layer disposed between the bottom layer and the top layer, and comprising a void configured to house a package content and in communication with the opening in the top layer;
a removable label affixed to the top layer covering the opening; and
a reservoir adjacent the opening and a gate therebetween, wherein the gate is configured to be removed with the label to establish a flow path between the reservoir and the opening.

16. A functional laminate package comprising:
a bottom layer;
a top layer comprising an opening;
an intermediate layer disposed between the bottom layer and the top layer, and comprising a void configured to house a package content and in communication with the opening in the top layer;
a removable label affixed to the top layer covering the opening; and
a second label affixed to the removable label, wherein both the removable label and the top layer comprise a kiss cut opening against the bottom of the second label.

* * * * *